(12) United States Patent
Pardee et al.

(10) Patent No.: US 7,153,700 B1
(45) Date of Patent: Dec. 26, 2006

(54) METHODS AND COMPOSITIONS FOR DIAGNOSING AND PREDICTING THE BEHAVIOR OF CANCER

(75) Inventors: Arthur B. Pardee, Brookline, MA (US); Heide L. Ford, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/647,115

(22) PCT Filed: Mar. 26, 1999

(86) PCT No.: PCT/US99/06679

§ 371 (c)(1),
(2), (4) Date: Jan. 11, 2001

(87) PCT Pub. No.: WO99/49084

PCT Pub. Date: Sep. 30, 1999

(51) Int. Cl.
*G01N 33/53* (2006.01)
*C12Q 1/68* (2006.01)

(52) U.S. Cl. .............................. 436/501; 436/518; 435/6

(58) Field of Classification Search .................. 435/7.1, 435/6, 7.23; 536/24.33
See application file for complete search history.

(56) References Cited

OTHER PUBLICATIONS

Boucher, et al., 1996, Genomic, vol. 33 pp. 140-142.*
Ganguly, et al., 1997, Genet Test, 1(2):85-90.*
Grogan, et al., 1997 Oncologist, 2(4):208-222.*
Shantz and Pegg (Int J of Biochem and Cell Biol., 1999, vol. 31, pp. 107-122).*
McClean and Hill (Eur J of Cancer, 1993, vol. 29A, pp. 2243-2248).*
Fu et al (EMBO Journal, 1996, vol. 15, pp. 4392-4401).*
Tockman et al (Cancer Res., 1992, 52:2711s-2718s).*
Freshney (Culture of Animal Cells, A Manual of Basic Technique, Alan R. Liss, Inc., 1983, New York, p. 4).*
Dermer (Bio/Technology, 1994, 12:320).*
Alberts et al. (Molecular Biology of the Cell, 3rd edition, 1994, p. 465).*
The attached SIX1 (A-20) product information downloaded from url>>www.scbt.com on Oct. 1, 2003.*
Campbell, A. (1986, Monoclonal antibody technology, chapter 1 only, Elsevier Science Publishers B.V., Netherlands).*
Chariot, A. Detection of HOXA1 expression in human breast cancer. *Biochem. Biophys. Res. Commun.* May 1996 15;222(2):292-297.
Cillo, C. HOX genes in human cancers. *Invasion Metastasis.* 1994-95;14(1-6):38-49.
Ford, H.L. et al. Role of the HSIX1 homeobox gene in the cell cycle and in cancer. *Cell and Tumor Biology.* Mar. 1998;39:650 Abstr. #4428.
Ford, H.L. et al. Abrogation of the $G_2$ cell cycle checkpoint associated with overexpression of HSIX1: a possible mechanism of breast carcinogenesis. *Proc. Natl. Acad. Sci. U. S. A.* Oct. 13, 1998;95(21):12608-12613.
Lawrence, H.J. et al. The role of HOX homeobox genes in normal and leukemic hematopoiesis. *Stem Cells.* May 1996;14(3):281-291.
Oliver, G. et al. Homeobox genes and connective tissue patterning. *Development.* Mar. 1995;121(3):693-705.
Spitz, F. et al. Expression of myogenin during embryogenesis is controlled by Six/sine oculis homeoproteins through a conserved MEF3 binding site. *Proc. Natl. Acad. Sci. U. S. A.* Nov. 24,1998;95(24):14220-14225.
Stuart, E.T. et al. PAX genes: what's new in developmental biology and cancer? *Hum. Mol. Genet.* 1995;4 Spec No. 1717-1720.
GenBank Acc. No. X91868; *H.sapiens* mRNA for SIX1 protein.
GenBank Acc. No. 1246761; six1 gene product.

* cited by examiner

*Primary Examiner*—Misook Yu
(74) *Attorney, Agent, or Firm*—Foley Hoag, LLP

(57) ABSTRACT

The present invention relates to methods for detecting the presence of SIX1 protein or nucleic acid in a biological sample in which a biological sample is contacted with an agent capable of detecting SIX1 protein or mRNA such that the presence of SIX1 is detected in the biological sample. Diagnostic and prognostic methods utilizing HSIX1 as an indicator of cancer and cancer progression are also provided. Compositions and kits for detecting the presence of SIX1 in a biological sample are also described.

26 Claims, 8 Drawing Sheets

*Figure 1*

```
   1 GGTAGCAGCA TCCACCGGGC GGGAGGTCGG AGGCAGCAAG GCCTTAAAGG CTACTGAGTG
  61 CGCCGGCCGT TCCGTGTCCA GAACCTCCCC TACTCCTCCG CCTTCTCTTC CTTGGCCGCC
 121 CACCGCCAAG TTCCGACTCC GGTTTTCGCC TTTGCAAAGC CTAAGGAGGA GGTTAGGAAC
 181 AGCCGCGCCC CCCTCCCTGC GGCCGCCGCC CCCTGCCTCT CGGCTCTGCT CCCTGCCGCG
 241 TGCGCCTGGG CCGTGCGCCC CGGCAGGCGC CAGCCATGTC GATGCTGCCG TCGTTTGGCT
 301 TTACGCAGGA GCAAGTGGCG TGCGTGTGCG AGGTTCTGCA GCAAGGCGGA AACCTGGAGC
 361 GCCTGGGCAG GTTCCTGTGG TCACTGCCCG CCTGCGACCA CCTGCACAAG AACGAGAGCG
 421 TACTCAAGGC CAAGGCGGTG GTCGCCTTCC ACCGCGGCAA CTTCCGTGAG CTCTACAAGA
 481 TCCTGGAGAG CCACCAGTTC TCGCCTCACA ACCACCCCAA ACTGCAGCAA CTGTGGCTGA
 541 AGGCGCATTA CGTGGAGGCC GAGAAGCTGC GCGGCCGACC CCTGGGCGCC GTGGGCAAAT
 601 ATCGGGTGCG CCGAAAATTT CCACTGCCGC GCACCATCTG GGACGGCGAG GAGACCAGCT
 661 ACTGCTTCAA GGAGAAGTCG AGGGGTGTCC TGCGGGAGTG GTACGCGCAC AATCCCTACC
 721 CATCGCCGCG TGAGAAGCGG GAGCTGGCCG AGGCCACCGG CCTCACCACC ACCCAGGTCA
 781 GCAACTGGTT TAAGAACCGG AGGCAAAGAG ACCGGGCCGC GGAGGCCAAG GAAAGGGAGA
 841 ACACCGAAAA CAATAACTCC TCCTCCAACA AGCAGAACCA ACTCTCTCCT CTGGAAGGGG
 901 GCAAGCCGCT CATGTCCAGC TCAGAAGAGG AATTCTCACC TCCCCAAAGT CCAGACCAGA
 961 ACTCGGTCCT TCTGCTGCAG GGCAATATGG GCCACGCCAG GAGCTCAAAC TATTCTCTCC
1021 CGGGCTTAAC AGCCTCGCAG CCCAGTCACG GCCTGCAGAC CCACCAGCAT CAGCTCCAAG
1081 ACTCTCTGCT CGGCCCCCTC ACCTCCAGTC TGGTGGACTT GGGGTCCTAA GTGGGGAGGG
1141 ACTGGGGCCT CGAAGGGATT CCTGGAGCAG CAACCACTGC AGCGACTAGG GACACTTGTA
1201 AATAGAAATC AGGAACATTT TTGCAGCTTG TTTCTGGAGT TGTTTGCGCA TAAAGGAATG
1261 GTGGACTTTC ACAAATATCT TTTTAAAAAT CAAAACCAAC AGCGATCTCA AGCTTAATCT
1321 CCTCTTCTCT CCAACTCTTT CCACTTTTGC ATTTTCCTTC CCAATGCAGA GATCAGGG
```

```
   1 MSMLPSFGFT QEQVACVCEV LQQGGNLERL GRFLWSLPAC DHLHKNESVL KAKAVVAFHR
  61 GNFRELYKIL ESHQFSPHNH PKLQQLWLKA HYVEAEKLRG RPLGAVGKYR VRRKFPLPRT
 121 IWDGEETSYC FKEKSRGVLR EWYAHNPYPS PREKRELAEA TGLTTTQVSN WFKNRRQRDR
 181 AAEAKERENT ENNNSSSNKQ NQLSPLEGGK PLMSSSEEEF SPPQSPDQNS VLLLQGNMGH
 241 ARSSNYSLPG LTASQPSHGL QTHQHQLQDS LLGPLTSSLV DLGS
```

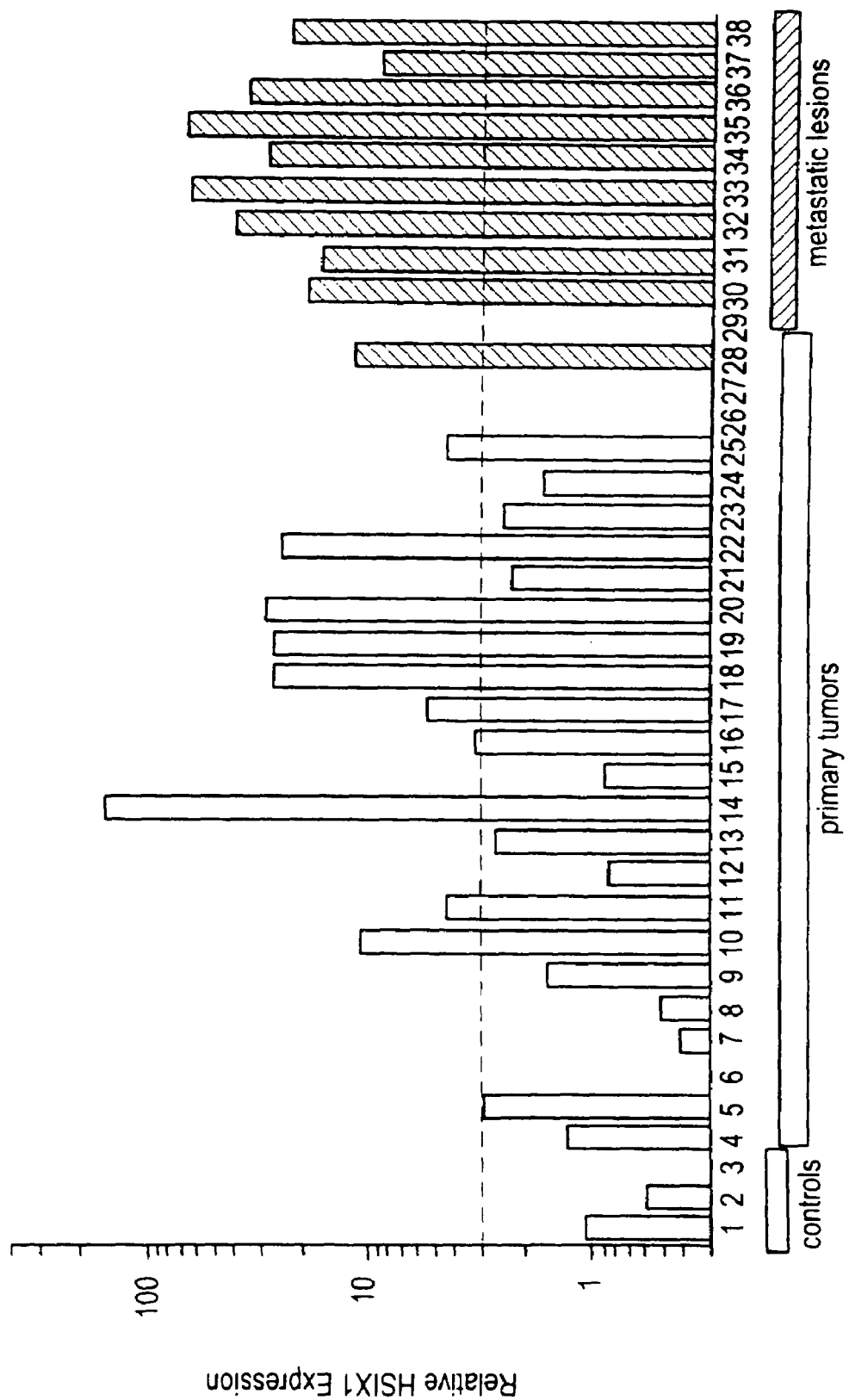

SEQUENCE LISTING

<160> NUMBER OF SEQ ID NOS: 6

<210> SEQ ID NO 1
<211> LENGTH: 1378
<212> TYPE: DNA
<213> ORGANISM: Homo sapiens
<220> FEATURE:
<221> NAME/KEY: CDS
<222> LOCATION: (276)...(1127)

<400> SEQUENCE: 1
ggtagcagca tccaccgggc gggaggtcgg aggcagcaag gccttaaagg ctactgagtg    60

-continued

```
cgccggccgt tccgtgtcca gaacctcccc tactcctccg ccttctcttc cttggccgcc      120
caccgccaag ttccgactcc ggttttcgcc tttgcaaagc ctaaggagga ggttaggaac      180
agccgcgccc ccctccctgc ggccgccgcc ccctgcctct cggctctgct ccctgccgcg      240
tgcgcctggg ccgtgcgccc cggcaggcgc cagcc atg tcg atg ctg ccg tcg         293
                                        Met Ser Met Leu Pro Ser
                                        1               5 ttt ggc ttt acg cag gag caa gtg gcg tgc gtg tgc gag gtt ctg cag        341
Phe Gly Phe Thr Gln Glu Gln Val Ala Cys Val Cys Glu Val Leu Gln
            10                  15                  20 caa ggc gga aac ctg gag cgc ctg ggc agg ttc ctg tgg tca ctg ccc        389
Gln Gly Gly Asn Leu Glu Arg Leu Gly Arg Phe Leu Trp Ser Leu Pro
        25                  30                  35 gcc tgc gac cac ctg cac aag aac gag agc gta ctc aag gcc aag gcg        437
Ala Cys Asp His Leu His Lys Asn Glu Ser Val Leu Lys Ala Lys Ala
    40                  45                  50 gtg gtc gcc ttc cac cgc ggc aac ttc cgt gag ctc tac aag atc ctg        485
Val Val Ala Phe His Arg Gly Asn Phe Arg Glu Leu Tyr Lys Ile Leu
55                  60                  65                  70 gag agc cac cag ttc tcg cct cac aac cac ccc aaa ctg cag caa ctg        533
Glu Ser His Gln Phe Ser Pro His Asn His Pro Lys Leu Gln Gln Leu
                75                  80                  85 tgg ctg aag gcg cat tac gtg gag gcc gag aag ctg cgc ggc cga ccc        581
Trp Leu Lys Ala His Tyr Val Glu Ala Glu Lys Leu Arg Gly Arg Pro
            90                  95                  100 ctg ggc gcc gtg ggc aaa tat cgg gtg cgc cga aaa ttt cca ctg ccg        629
Leu Gly Ala Val Gly Lys Tyr Arg Val Arg Arg Lys Phe Pro Leu Pro
        105                 110                 115 cgc acc atc tgg gac ggc gag gag acc agc tac tgc ttc aag gag aag        677
Arg Thr Ile Trp Asp Gly Glu Glu Thr Ser Tyr Cys Phe Lys Glu Lys
    120                 125                 130 tcg agg ggt gtc ctg cgg gag tgg tac gcg cac aat ccc tac cca tcg        725
Ser Arg Gly Val Leu Arg Glu Trp Tyr Ala His Asn Pro Tyr Pro Ser
135                 140                 145                 150 ccg cgt gag aag cgg gag ctg gcc gag gcc acc ggc ctc acc acc acc        773
Pro Arg Glu Lys Arg Glu Leu Ala Glu Ala Thr Gly Leu Thr Thr Thr
                155                 160                 165 cag gtc agc aac tgg ttt aag aac cgg agg caa aga gac cgg gcc gcg        821
Gln Val Ser Asn Trp Phe Lys Asn Arg Arg Gln Arg Asp Arg Ala Ala
            170                 175                 180 gag gcc aag gaa agg gag aac acc gaa aac aat aac tcc tcc tcc aac        869
Glu Ala Lys Glu Arg Glu Asn Thr Glu Asn Asn Asn Ser Ser Ser Asn
        185                 190                 195 aag cag aac caa ctc tct cct ctg gaa ggg ggc aag ccg ctc atg tcc        917
Lys Gln Asn Gln Leu Ser Pro Leu Glu Gly Gly Lys Pro Leu Met Ser
    200                 205                 210 agc tca gaa gag gaa ttc tca cct ccc caa agt cca gac cag aac tcg        965
Ser Ser Glu Glu Glu Phe Ser Pro Pro Gln Ser Pro Asp Gln Asn Ser
215                 220                 225                 230 gtc ctt ctg ctg cag ggc aat atg ggc cac gcc agg agc tca aac tat       1013
Val Leu Leu Leu Gln Gly Asn Met Gly His Ala Arg Ser Ser Asn Tyr
                235                 240                 245 tct ctc ccg ggc tta aca gcc tcg cag ccc agt cac ggc ctg cag acc       1061
Ser Leu Pro Gly Leu Thr Ala Ser Gln Pro Ser His Gly Leu Gln Thr
            250                 255                 260 cac cag cat cag ctc caa gac tct ctg ctc ggc ccc ctc acc tcc agt       1109
His Gln His Gln Leu Gln Asp Ser Leu Leu Gly Pro Leu Thr Ser Ser
        265                 270                 275
```

```
ctg gtg gac ttg ggg tcc taagtgggga gggactgggg cctcgaaggg    1157
Leu Val Asp Leu Gly Ser
    280 attcctggag cagcaaccac tgcagcgact agggacactt gtaaatagaa atcaggaaca    1217 tttttgcagc ttgtttctgg agttgtttgc gcataaagga atggtggact ttcacaaata    1277 tcttttaaa aatcaaaacc aacagcgatc tcaagcttaa tctcctcttc tctccaactc    1337 tttccactt tgcattttcc ttcccaatgc agagatcagg g    1378
```

<210> SEQ ID NO 2
<211> LENGTH: 284
<212> TYPE: PRT
<213> ORGANISM: Homo sapiens

<400> SEQUENCE: 2

```
Met Ser Met Leu Pro Ser Phe Gly Phe Thr Gln Glu Gln Val Ala Cys
  1               5                  10                  15

Val Cys Glu Val Leu Gln Gln Gly Gly Asn Leu Glu Arg Leu Gly Arg
             20                  25                  30

Phe Leu Trp Ser Leu Pro Ala Cys Asp His Leu His Lys Asn Glu Ser
         35                  40                  45

Val Leu Lys Ala Lys Ala Val Val Ala Phe His Arg Gly Asn Phe Arg
     50                  55                  60

Glu Leu Tyr Lys Ile Leu Glu Ser His Gln Phe Ser Pro His Asn His
 65                  70                  75                  80

Pro Lys Leu Gln Gln Leu Trp Leu Lys Ala His Tyr Val Glu Ala Glu
                 85                  90                  95

Lys Leu Arg Gly Arg Pro Leu Gly Ala Val Gly Lys Tyr Arg Val Arg
            100                 105                 110

Arg Lys Phe Pro Leu Pro Arg Thr Ile Trp Asp Gly Glu Glu Thr Ser
            115                 120                 125

Tyr Cys Phe Lys Glu Lys Ser Arg Gly Val Leu Arg Glu Trp Tyr Ala
        130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
            180                 185                 190

Asn Asn Ser Ser Asn Lys Gln Asn Gln Leu Ser Pro Leu Glu Gly
            195                 200                 205

Gly Lys Pro Leu Met Ser Ser Glu Glu Glu Phe Ser Pro Pro Gln
        210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
        275                 280
```

<210> SEQ ID NO 3
<211> LENGTH: 11
<212> TYPE: DNA
<213> ORGANISM: Artificial Sequence -continued

```
<220> FEATURE:
<223> OTHER INFORMATION: primer

<400> SEQUENCE: 3
tgccgaagct c                                                          11

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
tgccgaagct tgcagcga                                                   18

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
atgtcgatgc tgccgtcgtt t                                               21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cacttaggac cccaagtcca c                                               21
```

METHODS AND COMPOSITIONS FOR DIAGNOSING AND PREDICTING THE BEHAVIOR OF CANCER

BACKGROUND OF THE INVENTION

Today, cancer is known to be one of the leading causes of mortality and morbidity among men and women. In particular, breast cancer is believed to be the leading cause of death among women (Harris, el al. (1992) *New Engl. J. Med* 327: 319–28; Harris, et al. (1992) *New Engl. J. Med.* 327: 390–8: Harris, et al. (1992) *New Engl. J. Med.* 327: 473–80; and McGuire and Clark (1992) *New Engl. J. Med.* 326: 1756–61). The development of cancer is accompanied by a number of genetic changes (For review see Porter-Jordan. (1994) *Hematol. Oncol Clin. N. Am.* 8:73). Such changes include gross chromosomal alterations as well as loss of genetic markers (Devilee et al. (1994) *Biochim. Biophys. Acta* 1198:113 and Callahan et al.(1993) *J. Cell Biochem. Suppl.* 17:167). For example, the progression of breast neoplasia has also been shown to result in qualitative and quantitative changes in expression of previously identified genes that encode growth factors and their receptors (Zajchowski et al. (1988) *Cancer Res.* 48:7041), structural proteins (Trask et al. (1990) *Proc. Natl. Acad. Sci.* 87:2319), second messenger proteins (Ohuchi el al.(1986) *Cancer Res.* 26:251 1), and transcription factors (Harris (1992) *Adv. Cancer Res.* 59:69). Furthermore, novel genes have been identified whose increased expression can be correlated with the occurrence of breast tumors (e.g., mammaglobin, Watson and Fleming, U.S. Pat. No. 5,668,267).

Although progress has been made in the identification of various potential breast cancer marker genes, as well as other biomolecular markers of cancer (e.g., Prostate-Specific Antigen in the case of Prostate cancer) there remains a continuing need for new marker genes along with their expressed proteins that can be used to specifically and selectively identify the appearance and pathogenic development of cancer in a patient.

SUMMARY OF THE INVENTION

Briefly, the present invention relates to methods for diagnosing cancer, for example, breast, colon, lung, or cervical cancer, in a subject in which the presence of human SIX1 (HSIX1) homeobox gene sequences bears a positive correlation to the existence of malignant disease. The present invention is based, at least in part, on the demonstration of an aberrant expression of the HSIX1 homeobox gene in primary breast cancers and metastatic lesions and in cells isolated from lung, colorectal, and cervical tumors, as well as from subjects having chronic myelogenous leukemia. The present invention further relates to compositions of molecular probes which can be utilized in such diagnostic methods.

Accordingly, one aspect of the invention pertains to methods for detecting the presence of SIX1 in a biological sample. In a preferred embodiment, the method involves contacting a biological sample (e.g., a tissue or tumor sample or isolate of such a sample) with an agent capable of detecting SIX1 protein or nucleic acid (e.g., mRNA or cDNA) molecule such that the presence of SIX1 is detected in the biological sample. The agent can be, for example, a labeled or labelable nucleic acid probe capable of hybridizing to a SIX1 nucleic acid molecule or a labeled or labelable antibody capable of binding to SIX1 protein.

Another aspect of the invention features a method of determining the metastatic potential of a tumor which involves contacting a sample of the tumor (or isolate) with an agent capable of detecting SIX1 polypeptide or mRNA such that the presence of SIX1 polypeptide or mRNA is detected in the tumor sample or isolate, thereby determining the metastatic potential of the tumor. Yet another aspect of the invention features a prognostic method for determining whether a subject is at risk for developing cancer which involves contacting a biological sample obtained from the subject (or isolate of the sample) with an agent capable of detecting SIX1 polypeptide or mRNA such that the presence of SIX1 polypeptide or mRNA is detected in the biological sample or isolate, thereby determining whether the subject is at risk for developing cancer. Another aspect of the invention features a method for diagnosis of a tumor which involves contacting a tumor sample (or isolate) with an agent capable of detecting SIX1 polypeptide or mRNA such that the presence of SIX1 polypeptide or mRNA is detected in the biological sample or isolate, thereby diagnosing the tumor. Yet another aspect of the invention features a method of diagnosing cancer in a subject which involves contacting a biological sample obtained from the subject (or isolate of the sample) with an agent capable of detecting SIX1 polypeptide or mRNA such that the presence of SIX1 polypeptide or mRNA is detected in the biological sample or isolate, thereby diagnosing cancer in the subject. Kits for detecting SIX1 in a biological sample are also within the scope of the invention.

BRIEF DESCRIPTION OF THE DRAWINGS

FIG. 1 is the complete cDNA sequence and deduced amino acid sequence of human SIX1 (SEQ ID NOs:1 and 2, respectively).

FIG. 2A depicts 3H-thymidine incorporation following release from mimosine arrest showing progression of 21PT cells through S-phase. FIG. 2B is a photograph showing a section of a differential display gel demonstrating the differential expression of 6A (subsequently identified as HSIX1) in S-phase. FIG. 2C is a photograph of a Northern blot confirming the differential expression of HSIX1 throughout S-phase of 21PT cells. RNA was isolated from cells following release from mimosine arrest and Northern blot analysis was performed with the HSIX1 cDNA probe. Bottom panel shows EtBr staining as a loading control.

indicate lysates from mock transfected MCF7 cells. Antibody dilutions are indicated below respective pairs of lanes.

Figure 6:
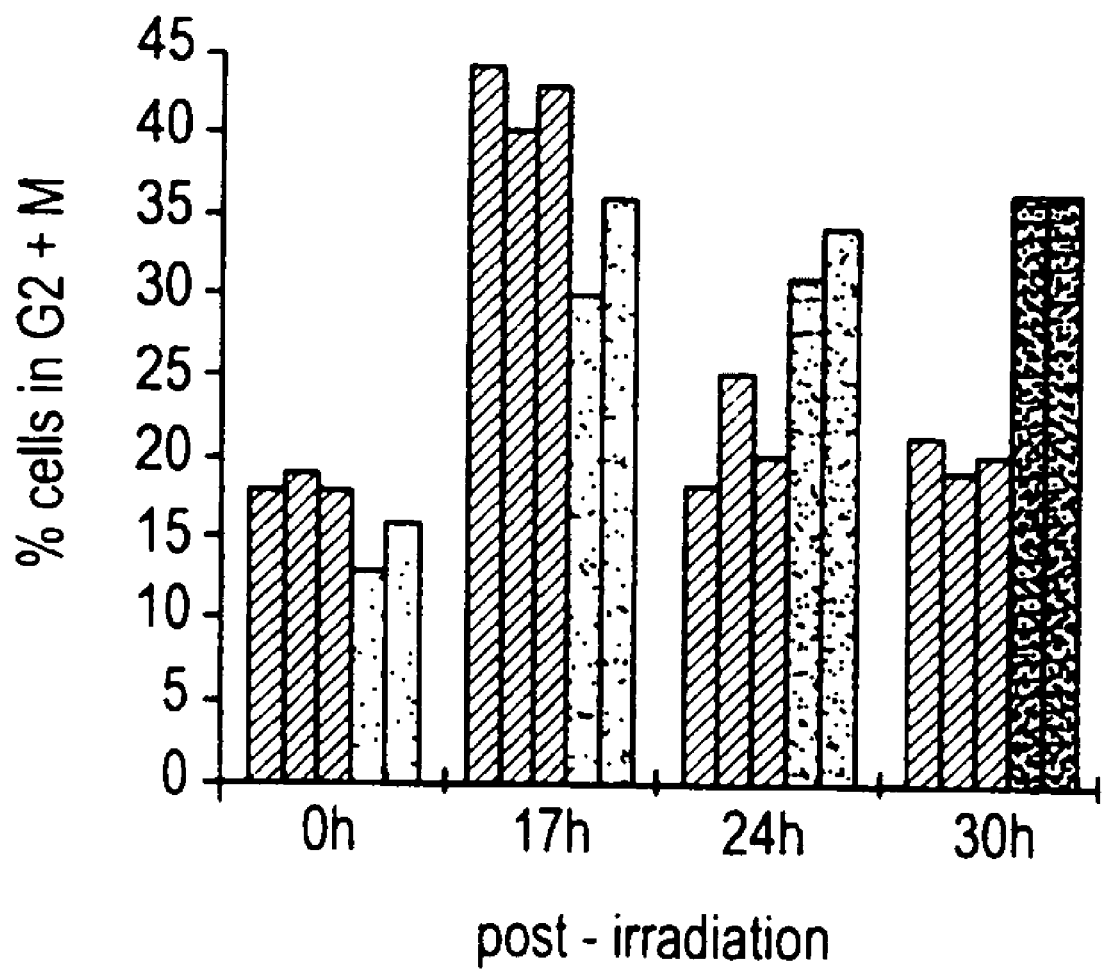

FIG. 6 demonstrates that HSIX1 overexpression abrogates the G2 cell cycle checkpoint. The graph shows a summary of the percentage of either HSIX1-transfectanted cells or control cells (CAT transfectants) in G2 at various times after X-ray irradiation. Stippled bars indicate the HSIX overexpressors (A1, A8, and A13). The shaded bars indicate CAT-transfected controls (B 1 and B3).

DETAILED DESCRIPTION OF THE INVENTION

The invention is based, at least, in part on the discovery that the human SIX1 gene ("HSIX1"), a known homoebox gene, is aberrantly expressed (e.g., overexpressed) in tumorigenic cells. As used herein, HSIX1 refers to a gene obtained from human adult skeletal muscle (Boucher el al. (1996) *Genomics* 33:140–142) whose mouse counterpart has been implicated in the development of limb tendons (Oliver et al. (1995) *Development* 121:693–705). HSIX1 is a member of a family of genes termed homeobox genes. As used herein "homeobox genes" include genes which encode a family of proteins, termed homeodomain-containing proteins, which act as transcription factors that regulate the coordinated expression of genes involved in both development and differentiation. Homeobox genes were identified initially in *Drosophila*, where they were found to be important in the control of sequence identity (Lewis (1978) *Nature* 276;565–570). Homeobox genes contain a common 183-nt sequence encoding a 61-aa domain that is responsible for DNA binding (McGinnis and Krumlauff (1992) *Cell* 68:283–302). They are postulated to act as a network of transcriptional regulators effecting cell—cell communication during normal development, alterations of which may contribute to the neoplastic phenotype. Recently, homeobox genes, including members of the Hox and Pax families have been identified as oncogenic transcription factors (Lawrence et al. (1996) *Stem Cell* 14:281–291 and Stuart and Gruss (1995) *Human Mol. Genet*. 4:1717–1720). Homeobox genes are often translocated to produce a chimeric protein with a new function, particularly in leukemias (Cillo (1994) *Invasion Metastasis* 14:38–49). However, others retain their wild type function and are overexpressed (Lawrence et al. Cillo, and Stuart and Gruss, supra). In addition to leukemias, recent studies have demonstrated homeobox gene involvement in solid tumors such as breast, kidney, lung and colon (Cillo, supra).

The present invention is further based, at least in part on the identification of HSIX1 cDNA by its differential expression in cell cycle synchronized 21PT mammary adenocarcinoma cell line (a cell line derived from a patient who had an infiltrating and intraductal mammary adenocarcinoma) using the differential display method. Direct sequencing of one differentially-expressed cDNA revealed its identity as HSIX1. Further analysis revealed that HSIX1 mRNA expression was very low in the first half of S phase and increased as 21PT cells are completing S phase. HSIX1 expression was also detected in other cell lines derived from the same patient including 21NT. 21MT-1 and 21MT-2. The 21PT and 21NT cell lines were derived from a primary tumor, whereas the 21MT-1 and 21MT-2 cells lines were established from a metastatic pleural effusion. By contrast, HSIX1 expression was not detected in a normal breast cell line. 70N (Band and Sager (1989) *Proc. Natl. Acad. Sci. USA* 86:1249–1253).

The invention is further based on the discovery that the HSIX1 homeobox protein functions in a cell cycle-regulated manner and acts to abrogate G2 cell cycle arrest. In particular, cells which overexpress HSIX1 progress through X-ray irradiation-induced G2 arrest at a more rapid rate than control cells (e.g., normal cells). Furthermore, continued passaging of 21PT cells which constitutivly overexpress HSIX1 leads to ploidy changes over extended periods of time.

The molecular weight of HSIX1 appears to be unchanged in 21PT cells as compared to normal cells, suggesting that no gross genetic alterations exist. However, a translocation may occur upstream of the transcription start site resulting in aberrant expression, or point mutations or small deletions/insertions may exist in the gene. Alternatively, overexpression of wild type HSIX1 mRNA may contribute to the tumorigenic phenotype, consistent with a model proposed by Sager et al., which hypothesizes that tumorigenesis is not only the result of genetic mutations, but also of overexpression of wild type genes. In fact, direct sequencing of HSIX1 from 21PT cells resulted in wild type HSIX DNA sequence. The fact that SIX1 overexpression correlates with both the tumorigenic phenotype as well as with abrogation of the G2 cell cycle check point, indicates its utility as a growth-related or aberrant growth marker or marker of the tumorigenic phenotype.

Accordingly, the present invention features a method for detecting the presence of SIX1 in a biological sample (e.g., a tumor sample) involving contacting a biological sample with an agent (e.g., a nucleic acid probe or antibody) capable of detecting SIX1 protein or nucleic acid (e.g., mRNA or cDNA) such that the presence of SIX1 is detected in the biological sample.

As used herein, a "biological sample" refers to a sample of biological material obtained from a subject, preferably a human subject, or present within a subject, preferably a human subject, including a tissue, tissue sample, or cell sample (e.g., a tissue biopsy, for example, an aspiration biopsy, a brush biopsy, a surface biopsy, a needle biopsy, a punch biopsy, an excision biopsy, an open biopsy, an incision biopsy or an endoscopic biopsy), tumor, tumor sample, or biological fluid (e.g., blood, serum, lymph, spinal fluid).

As used herein, a "tissue sample" refers to a portion, piece, part, segment, or fraction of a tissue which is obtained or removed from an intact tissue of a subject, preferably a human subject. For example, tissue samples can be obtained from the pancreas, stomach, liver, secretory gland, bladder, lung, skin, prostate gland, breast ovary, cervix, uterus, brain, eye, connective tissue, bone, muscles or vasculature. In a preferred embodiment, the biological sample is a breast tissue sample. In another embodiment, the biological sample is a tissue sample, provided that it is not a breast tissue sample. In yet another embodiment, the biological sample is a tumor sample (e.g., a tumor biopsy).

As used herein, a "tumor sample" refers to a portion, piece, part, segment, or fraction of a tumor, for example, a tumor which is obtained or removed from a subject (e.g., removed or extracted from a tissue of a subject), preferably a human subject. A tumor sample can be obtained, for example, from a lung carcinoma, a colon carcinoma, a cervical carcinoma, an adenocarcinoma, a melanoma, a leukemia, a lymphoma, a glioma, a neuroblastoma, a retinoblastoma, and a sarcoma. In one embodiment, the tumor sample is obtained from a breast tumor (e.g., a breast tumor sample). In another embodiment, the tumor sample is obtained from a tumor, provided that the tumor is not a breast tumor. In yet another embodiment, the tumor sample is obtained from a primary tumor (e.g., is a primary tumor sample). In another embodiment, the biological sample is obtained metastatic lesion (e.g., is a metastatic lesion sample).

As defined herein, a "primary tumor" is a tumor appearing at a first site within the subject and can be distinguished from a "metastatic tumor" which appears in the body of the subject at a remote site from the primary tumor. As used herein, a "metastatic tumor" is a tumor resulting from the dissemination of cells from a primary tumor by the lymphatics or blood vessels or by direct extension through serum-containing or serum-producing cavities or other spaces.

The present invention also encompasses the use of isolates of a biological sample in the methods of the invention. As used herein, an "isolate" of a biological sample (e.g., an isolate of a tissue or tumor sample) refers to a material or composition (e.g., a biological material or composition) which has been separated, derived, extracted, purified or isolated from the sample and preferably is substantially free of undesirable compositions and/or impurities or contaminants associated with the biological sample. Preferred isolates include, but are not limited to, DNA (e.g., cDNA or genomic DNA). RNA (e.g., mRNA), and protein (i.e., purified protein, protein extracts, polypeptides). Additional preferred isolates include cells as well as biological fluids (e.g., blood, serum, lymph, spinal fluid).

The present invention features agents which are capable of detecting SIX1 polypeptide or mRNA such that the presence of SIX is detected. As defined herein, an "agent" refers to a substance which is capable of identifying or detecting SIX in a biological sample (e.g., identifies or detects SIX mRNA, SIX DNA, SIX protein, SIX activity). In one embodiment, the agent is a labeled or labelable antibody which specifically binds to SIX1 polypeptide. As used herein, the phrase "labeled or labelable" refers to the attaching or including of a label (e.g., a marker or indicator) or ability to attach or include a label (e.g., a marker or indicator). Markers or indicators include, but are not limited to, for example, radioactive molecules, colorimetric molecules, and enzymatic molecules which produce detectable changes in a substrate. In one embodiment the agent is an antibody which specifically binds to all or a portion of a SIX protein (e.g., hSIX1). As used herein, the phrase "specifically binds" refers to binding of, for example, an antibody to an epitope or antigen or antigenic determinant in such a manner that binding can be displaced or competed with a second preparation of identical or similar epitope, antigen or antigenic determinant. In an exemplary embodiment, the agent is an antibody which specifically binds to all or a portion of HSIX1 protein. In another embodiment, the agent is an antibody which specifically binds to all or a portion of a polypeptide selected from the group consisting of a polypeptide having the amino acid sequence of SEQ ID NO:2, a polypeptide comprising at least amino acids 183–284 of SEQ ID NO:2; and a polypeptide consisting of amino acids 183–284 of SEQ ID NO:2. In another embodiment, the antibody is a polyclonal antibody.

In yet another embodiment the agent is a labeled or labelable nucleic acid probe capable of hybridizing to SIX1 mRNA. For example, the agent can be an ioligonucleotide primer for the polymerase chain reaction which flank or lie within the nucleotide sequence encoding human SIX1. In a preferred embodiment, the biological sample being tested is an isolate, for example, RNA. In yet another embodiment, the isolate (e.g., the RNA) is subjected to an amplification process which results in amplification of SIX1 nucleic acid.

As defined herein, an "amplification process" is designed to strengthen, increase, or augment a molecule within the isolate. For example, where the isolate is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

The present invention is also based in part on the discovery that HSIX is expressed in approximately one-half of primary breast cancers and nine-tenths of metastatic breast cancer lesions. While normal adjacent breast, normal breast luminal cells, and normal breast myoepithelial cells demonstrated almost no HSIX1 expression, 44% of primary tumors and 90% of the metastatic lesions had elevated levels of HSIX1 mRNA. HSIX1 overexpression was likewise found in samples of lung tumors, when compared to adjacent normal lung tissue samples. Moreover, smaller scale analysis of several different tumor cell lines suggest that HSIX1 may be expressed in a wide variety of tumors in addition to breast and lung.

Accordingly, the invention further features diagnostic and prognostic methods useful in the detection and treatment of cancer, preferably breast cancer, described in detail herein. The invention further involves kits useful in the detection and treatment of cancer, described in detail herein. In one embodiment, the invention features a method of determining the metastatic potential of a tumor which involves contacting a sample of the tumor (or isolate) with an agent capable of detecting SIX1 polypeptide or mRNA such that the presence of SIX1 polypeptide or mRNA is detected in the tumor sample or isolate, thereby determining the metastatic potential of the tumor. Another aspect of the invention features a prognostic method for determining whether a subject is at risk for developing cancer which involves contacting a biological sample obtained from the subject (or isolate of the sample) with an agent capable of detecting SIX1 polypeptide or mRNA such that the presence of SIX1 polypeptide or mRNA is detected in the biological sample or isolate, thereby determining whether the subject is at risk for developing cancer.

As used herein, a subject "at risk for developing cancer" includes a subject which has been determined to have a higher probability of developing cancer when compared to an average representative of the population. A subject's "risk of developing cancer" can be based on an analysis of empirical criteria or on a persons pedigree.

Yet another aspect of the invention features a method for diagnosis of a tumor which involved contacting a tumor sample (or isolate) with an agent capable of detecting SIX1 polypeptide or mRNA such that the presence of SIX1 polypeptide or mRNA is detected in the biological sample or isolate, thereby diagnosing the tumor. Yet another aspect of the invention features a method of diagnosing cancer in a subject which involves contacting a biological sample obtained from the subject (or isolate of the sample) with an agent capable of detecting SIX1 polypeptide or mRNA such that the presence of SIX1 polypeptide or mRNA is detected in the biological sample or isolate thereby diagnosing cancer in the subject.

In another embodiment, the diagnostic methods of the present invention further involve determining the level of SIX1 polypeptide or mRNA in the sample or isolate. As used herein, the phrase "determining the level" includes measuring an amount (e.g., making a quantitative determination) or making a qualitative determination (e.g., a determination of the presence versus the absence of SIX protein or nucleic acid). In yet another embodiment, the diagnostic methods of the present invention involve comparing the level of SIX1 polypeptide or mRNA in the sample or isolate with the level of SIX1 polypeptide or mRNA in a control sample. As used herein, the phrase "comparing the level" includes evaluating, balancing or contrasting the amount or presence of, for example, SIX protein or nucleic acid in a first sample (e.g., a test sample) with the amount or presence of SIX protein or nucleic acid in a second sample (e.g., a control sample). In yet another embodiment, the diagnostic or prognostic methods further includes the step of forming a prognosis or forming a diagnosis.

Another feature of the present invention includes a kit for detecting the presence of SIX1 in a biological sample (or isolate of the sample) including a labeled or labelable agent capable of detecting SIX1 polypeptide or mRNA in a biological sample. In one embodiment, the kit further includes a means for determining the amount of SIX1 in the sample. In another embodiment, the agent of the kit is an antibody capable of specifically binding to SIX1 polypeptide. In yet another embodiment, the agent of the kit is a nucleic acid probe capable of hybridizing to SIX1 mRNA. In yet another embodiment, the kit further includes a means for comparing the amount of SIX1 in the sample with a standard. In yet another embodiment, the kit further includes directions for use.

Various aspects of the invention are described in further detail in the following subsections:

I. Isolated Nucleic Acid Molecules

One aspect of the invention involves isolated nucleic acid molecules that encode SIX1 or biologically active portions thereof, as well as nucleic acid fragments sufficient for use as hybridization probes to identify SIX1-encoding nucleic acid (e.g., SIX1 mRNA). As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA. An "isolated" nucleic acid molecule is free of sequences which naturally flank; the nucleic acid (i.e., sequences located at the 5' and 3' ends of the nucleic acid) in the genomic DNA of the organism from which the nucleic acid is derived. For example, in various embodiments, the isolated SIX1 nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a human mammary adenocarcinoma cell). Moreover, an "isolated" nucleic acid molecule, such as a cDNA molecule, may be free of other cellular material.

In a preferred embodiment, an isolated nucleic acid molecule of the invention comprises the nucleotide sequence shown in SEQ ID NO: 1. The sequence of SEQ ID NO: 1 corresponds to the human SIX1 cDNA. This cDNA comprises sequences encoding the SIX1 protein (i.e., "the coding region", from nucleotides 276 to 1130), as well as 5' untranslated sequences (nucleotides 1 to 275) and 3' untranslated sequences (nucleotides 1131 to 1378). Alternatively, the nucleic acid molecule may comprise only the coding region of SEQ ID NO: 1 (e.g., nucleotides 276 to 1130).

Moreover, the nucleic acid molecule of the invention can comprise only a portion of the coding region of SEQ ID NO, 1, for example a fragment encoding a biologically active portion of SIX1. The term "biologically active portion of SIX1" is intended to include portions of SIX1 that retain the ability to enhance cell cycle progression, abrogate the G2 cell cycle checkpoint (e.g., accelerate the progression of cells through G2), or promote aberrant growth (e.g., tumorigenesis). The ability of portions of SIX1 to inhibit cell cycle progression can be determined in standard cell cycle progression assays, for example using 3H-thymidine as an indicator of progression through S phase, propidium iodide staining and FACS analysis as an indicator of cells in G2/M phase of the cell cycle (described further below and in Examples 1 and 3). Nucleic acid fragments encoding biologically active portions of SIX1 can be prepared by isolating a portion of SEQ ID NO: 1, expressing the encoded portion of SIX1 protein or peptide (e.g., by recombinant expression in vitro as detailed below in Example 3) and assessing the ability of the encoded fragment to effect cell cycle progression.

The invention further encompasses nucleic acid molecules that differ from SEQ ID NO: 1 (and portions thereof) due to degeneracy of the genetic code and thus encode the same SIX1 protein as that encoded by SEQ ID NO: 1. Accordingly, in another embodiment, an isolated nucleic acid molecule of the invention has a nucleotide sequence encoding a protein having an amino acid sequence shown in SEQ ID NO: 2. Moreover, the invention encompasses nucleic acid molecules that encode biologically active portions of SEQ ID NO: 2.

A nucleic acid molecule having the nucleotide sequence of SEQ ID NO: 1, or a portion thereof can be isolated using standard molecular biology techniques and the sequence information provided herein. For example, a human SIX1 cDNA can be isolated from a mammary adenocarcinoma cell line cDNA library using all or portion of SEQ ID NO: 1 as a hybridization probe and standard hybridization techniques (e.g., as described in Sambrook, J., Fritsh, E. F., and Maniatis, T. *Molecular Cloning. A Laboratory Manual*, 2nd, ed., Cold Spring Harbor Laboratory, Cold Spring Harbor, N.Y., 1989). Moreover, a nucleic acid molecule encompassing all or a portion of SEQ ID NO: 1 can be isolated by the polymerase chain reaction using oligonucleotide primers designed based upon the sequence of SEQ ID NO: 1. For example, mRNA can be isolated from mammary adenocarcinoma cells (e.g., by the guanidinium-thiocyanate extraction procedure of Chirgwin et al. (1979) *Biochemistry* 18: 5294–5299) and CDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SIX1 nucleotide sequence can be prepared by standard synthetic techniques, e.g., using an automated DNA synthesizer.

In addition to the human SIX1 nucleotide sequence shown in SEQ ID NO: 1, it will be appreciated by those skilled in the art that DNA sequence polymorphisms that lead to changes in the amino acid sequences of SIX1 may exist within a population (e.g., the human population). Such genetic polymorphism in the SIX1 gene may exist among individuals within a population due to natural allelic variation. Such natural allelic variations can typically result in 1–5% variance in the nucleotide sequence of the a gene. Any and all such nucleotide variations and resulting amino acid polymorphisms in SIX1 that are the result of natural allelic variation and that do not alter the functional activity of SIX1 are intended to be within the scope of the invention. Moreover, nucleic acid molecules encoding SIX1 proteins from other species, and thus which have a nucleotide sequence which differs from the human sequence of SEQ ID NO: 1, are intended to be within the scope of the invention. Nucleic acid molecules corresponding to natural allelic variants and nonhuman homologues of the human SIX1 cDNA of the invention can be isolated based on their homology to the human SIX1 nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO: 1. In other embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%. and even more preferably at least 75% homologous to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6X sodium chloride/sodium citrate (SSC) at about 45° C. followed by one or more washes in 0.2X SSC, 0.1% SDS at 50–65° C. Preferably, an isolated nucleic acid molecule of the invention that hybridizes under stringent conditions to the sequence of SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human SIX1.

In addition to naturally-occurring allelic variants of the SIX1 sequence that may exist in the population, the skilled artisan will further appreciate that changes may be introduced by mutation into the nucleotide sequence of SEQ ID NO: 1, thereby leading to changes in the amino acid sequence of the encoded SIX1 protein, without altering the functional ability of the SIX1 protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of SIX1 (e.g., the sequence of SEQ ID NO: 2) without altering the activity of SIX1, whereas an "essential" amino acid residue is required for SIX1 activity. Amino acid residues of SIX1 that are strongly conserved among, for example, among members of the subfamily of homeobox genes that share a lysine within the DNA binding helix of the homeodomain (e.g., the Drosophila sine oculis (so) gene, the human myotonic dystrophy (DM)-associated homeodomain protein (DMHAP) and its murine homologue (Boucher et al. (1995) *Hum. Mol. Genet,* 4:1919–1925), the human SIX1 gene and its murine counterpart, and the murine SIX2 gene. (e.g., conserved among proteins whose amino acid sequences are aligned for comparison purposes) are predicted to be essential in SIX1 and thus are not likely to be amenable to alteration. Other amino acid residues, however, (e.g., those that are not conserved or only semi-conserved among members of the subfamily) may not be essential for SIX1 activity and thus are more likely to be amenable to alteration.

Accordingly, another aspect of the invention pertains to nucleic acid molecules encoding SIX1 proteins that contain changes in amino acid residues that are not essential for SIX1 activity , e.g., residues that are not conserved or only semi-conserved among members of the subfamily. Such SIX1 proteins differ in amino acid sequence from SEQ ID NO: 2 yet retain SIX1 activity. In one embodiment, the isolated nucleic acid molecule comprises a nucleotide sequence encoding a protein, wherein the protein comprises an amino acid sequence at least 60% homologous to the amino acid sequence of SEQ ID NO: 2 and retains SIX1 activity. Preferably, the protein encoded by the nucleic acid molecule is at least 70% homologous to SEQ ID NO: 2, more preferably at least 80% homologous to SEQ ID NO: 2, even more preferably at least 90% homologous to SEQ ID NO:2, and most preferably at least 95% homologous to SEQ ID NO: 2.

To determine the percent homology of two amino acid sequences (e.g., SEQ ID NO, 2 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., SEQ ID NO: 2) is occupied by the same amino acid residue as the corresponding position in the other sequence (e.g., a mutant form of SIX1), then the molecules are homologous at that position (i.e., as used herein amino acid "homology" is equivalent to amino acid "identity"). The percent homology between the two sequences is a function of the number of identical positions shared by the sequences (i.e., % homology=# of identical positions/total # of positions×100). Such an alignment can be performed using any one of a number of computer algorithms designed for such a purpose. A preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

An isolated nucleic acid molecule encoding a SIX1 protein homologous to the protein of SEQ ID NO: 2 can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g, glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in SIX1 is preferably replaced with another amino acid residue from the same side chain family. Alternatively, in another embodiment, mutations can be introduced randomly along all or part of a SIX1 coding sequence, such as by saturation mutagenesis, and the resultant mutants can be screened for SIX1 activity to identify mutants that retain SIX1 activity. Following mutagenesis of SEQ ID NO: 1, the encoded protein can be expressed recombinantly (e.g., as described in Example 3) and the SIX1 activity of the protein can be determined. Suitable assays for testing the activity of portions of SIX1 proteins and mutated SIX1 proteins are described in detail in Examples 1 and 3.

In addition to the nucleic acid molecules encoding SIX1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g. complementary to the coding strand of a double-stranded cDNA molecule or complementary to an mRNA sequence. Accordingly, an antisense nucleic acid can hydrogen bond to a sense nucleic acid.

The antisense nucleic acid can be complementary to an entire SIX1 coding strand, or to only a portion thereof In one embodiment, an antisense nucleic acid molecule is antisense to a "coding region" of the coding strand of a nucleotide sequence encoding SIX1. The term "coding region" refers to the region of the nucleotide sequence comprising codons which are translated into amino acid residues (e.g., the entire coding region of SEQ ID NO: 1 comprises nucleotides 276–1130). In another embodiment, the antisense nucleic acid molecule is antisense to a "noncoding region" of the coding strand of a nucleotide sequence encoding SIX1. The term "noncoding region" refers to 5' and 3' sequences which flank the coding region that are not translated into amino acids (i.e., also referred to as 5' and 3' untranslated regions).

Given the coding strand sequences encoding SIX1 disclosed herein (e.g., nucleotides 276–1130 of SEQ ID NO: 1), antisense nucleic acids of the invention can be designed according to the rules of Watson and Crick base pairing. The antisense nucleic acid molecule may be complementary to the entire coding region of SIX1 mRNA, but more preferably is an oligonucleotide which is antisense to only a portion of the coding or noncoding region of SIX1 mRNA. For example, the antisense oligonucleotide may be complementary to the region surrounding the translation start site of SIX1 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a SIX1-encoding nucleic acid can be designed based upon the nucleotide sequence of a SIX1 cDNA disclosed herein (i.e., SEQ ID NO: 1). For example, a derivative of a *Tetrahymena* L-19 IVS RNA can be constructed in which the base sequence of the active site is complementary to the base sequence to be cleaved in a SIX1-encoding mRNA. See for example Cech et al. U.S. Pat. No, 4,987,071; and Cech et al. U.S. Pat. No, 5,116,742. Alternatively, SIX1 mRNA can be used to select a catalytic RNA having a specific ribonuclease activity from a pool of RNA molecules. See for example Bartel, D. and Szostak, J. W. (1993) *Science* 261: 1411–1418.

II. Recombinant Expression Vectors and Host Cells

Another aspect of the invention pertains to vectors, preferably expression vectors, containing a nucleic acid encoding SIX1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel, *Gene Expression Technology. Methods in Enzymology* 185, Academic Press. San Diego, Calif.

(1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SIX1 proteins, mutant forms of SIX1, fusion proteins, etc.).

The recombinant expression vectors of the invention can be designed for expression of SIX1 in prokaryotic or eukaryotic cells. For example, SIX1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors typically serve three purposes, 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In a preferred embodiment, exemplified in Example 3, the coding sequence of the mature form of SIX1 (i.e., encompassing amino acids 1–284) is cloned into a pGEX expression vector to create a vector encoding a fusion protein comprising, from the N-terminus to the C-terminus, GST-thrombin cleavage site-SIX1. The fusion protein can be purified by affinity chromatography using glutathione-agarose resin. Recombinant SIX1 unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL2(DE3) or HMS174 (DE3) from a resident λ prophage harboring a T7 gn 1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res*, 20:2111–2118). Such alteration of nucleic acid sequences of the invention can be carried out by standard DNA synthesis techniques.

In another embodiment, the SIX1 expression vector is a yeast expression vector. Examples of vectors for expression in yeast *S. cerivisace* include pYepSec1 (Baldari, et al., (1987) *Embo J.* 6:229–234), pMFa (Kurjan and Herskowitz. (1982) *Cell* 30:933–943). pJRY88 (Schultz et al., (1987) *Gene* 54:113–123), and pYES2 (Invitrogen Corporation, San Diego, Calif.).

Alternatively, SIX1 can be expressed in insect cells using baculovirus expression vectors. Baculovirus vectors available for expression of proteins in cultured insect cells (e.g .., Sf9 cells) include the pAc series (Smith et al., (1983) *Mol. Cell Biol*, 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example. SIX1 protein may be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can he found in Sambrook et al. (*Molecular Cloning: A Laboratory Manual*, 2 nd Edition. Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding SIX1 or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SIX1 protein. Accordingly, the invention further provides methods for producing SIX1 protein using the host cells of the invention. In one embodiment, the method comprises culturing the host cell of invention (into which a recombinant expression vector encoding SIX1 has been introduced) in a suitable medium until SIX1 is produced. In another embodiment, the method further comprises isolating SIX1 from the medium or the host cell. Such an isolated SIX1 protein can be used, for example, to raise antibodies to a SIX1 protein for use in the diagnostic methods of the present invention (described further below).

III. Isolated SIX1 Proteins and Anti-SIX1 Antibodies

Another aspect of the invention pertains to isolated SIX1 proteins, and biologically active portions thereof as well as peptide fragments suitable as immunogens to raise anti-SIX1 antibodies. The invention provides an isolated preparation of SIX1, or a biologically active portion thereof. An "isolated" protein is substantially free of cellular material or culture medium when produced by recombinant DNA techniques, or chemical precursors or other chemicals when chemically synthesized. In a preferred embodiment, the SIX1 protein has an amino acid sequence shown in SEQ ID NO: 2. In other embodiments., the SIX1 protein is substantially homologous to SEQ ID NO: 2 and retains the functional activity of the protein of SEQ ID NO: 2 yet differs in amino acid sequence due to natural allelic variation or mutagenesis, as described in detail in subsection I above. Accordingly, in another embodiment, the SIX1 protein is a protein which comprises an amino acid sequence at least 60% homologous to the amino acid sequence of SEQ ID NO: 2 and retains a SIX1 activity. Preferably, the protein is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

An isolated SIX1 protein may comprise the entire amino acid sequence of SEQ ID NO: 2 (i.e., amino acids 1–284), a biologically active portion thereof, or an immunogenic portion thereof For example, an immunogenic portion of SIX1 can comprise portion of SIX1 in which hydrophobic, and thus predicted to comprise an surface portion of a SIX1 protein. An immunogenic portion can also comprise all or a portion of a SIX1 protein which is unique to SIX1 (e.g., does not share significant homology with other homeobox proteins, thereby reducing the risk of cross-reactivity with non-SIX1 proteins). Accordingly, in one embodiment, an immunogenic portion of a SIX1 protein includes all or a portion of human SIX1 (SEQ ID NO:2) from about amino acids 183 to 284. Moreover, other biologically active and/or immunogenic portions, in which other regions of the protein are deleted, can be prepared by recombinant techniques and evaluated for SIX1 activity as described in detail above or alternatively, tested for immunogenicity.

SIX1 proteins are preferably produced by recombinant DNA techniques. For example, a nucleic acid molecule encoding all or a portion of the protein is cloned into an expression vector (as described above), the expression vector is introduced into a host cell (as described above) and the SIX1 protein or portion thereof is expressed in the host cell. The SIX1 protein or portion thereof can then be isolated from the cells by an appropriate purification scheme using standard protein purification techniques. In an exemplary embodiment, a nucleic acid molecule comprising nucleotides 1 to 1130 of SEQ ID NO:1 is cloned into an expression vector. In another embodiment, a nucleic acid molecule comprising nucleotides 822 to 1130 is cloned into an expression vector. Alternative to recombinant expression, a SIX1 protein or polypeptide can be synthesized chemically using standard peptide synthesis techniques. Moreover, native SIX1 protein can be isolated from cells (e.g., cultured human mammary adenocarcinoma cells), for example using an anti-SIX1 antibody (discussed further below).

The invention also provides SIX1 fusion proteins. As used herein, a SIX1 "fusion protein" comprises a SIX1 polypeptide operatively linked to a non-SIX1 polypeptide. A "SIX1 polypeptide" refers to a polypeptide having an amino acid sequence corresponding to SIX1, whereas a "non-SIX1 polypeptide" refers to a polypeptide having an amino acid sequence corresponding to another protein. Within the fusion protein, the term "operatively linked" is intended to indicate that the SIX1 polypeptide and the non-SIX1 polypeptide are fused in-frame to each other. The non-SIX1 polypeptide may be fused to the N-terminus or C-terminus of the SIX1 polypeptide. In one embodiment, a non-SIX1 polypeptide (e.g., GST) can be fused to the C-terminus of the SIX1 polypeptide (e.g., amino acids 183 to 284 of SEQ ID NO:2). Such fusion proteins can facilitate the purification of recombinant SIX1 (see, for example, the fusion proteins described in Example 5). In another embodiment, the fusion protein is a SIX1 protein containing a heterologous signal sequence at its N-terminus. In certain host cells (e.g., mammalian host cells), expression and/or secretion of SIX1 may be increased through use of a heterologous signal sequence.

Preferably, a SIX1 fusion protein of the invention is produced by standard recombinant DNA techniques. For example. DNA fragments coding for the different polypeptide sequences are ligated together in-frame in accordance with conventional techniques, for example employing blunt-ended or stagger-ended termini for ligation, restriction enzyme digestion to provide for appropriate termnini, filling in of cohesive ends as appropriate, alkaline phosphatase treatment to avoid undesirable joining, and enzymatic ligation. In one embodiment, a DNA fragment encoding a non-SIX1 polypeptide (e.g GST) is ligated in frame with a DNA fragment encoding a portion of SIX1 (e.g., including all or a portion of SEQ ID NO:2, for example, amino acids 183 to 284 of SEQ ID NO:2). In another embodiment, the fusion gene can be synthesized by conventional techniques including automated DNA synthesizers. Alternatively. PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons, 1992). Moreover, many expression vectors are commercially available that already encode a fusion moiety (e.g., a GST polypeptide). A SIX1-encoding nucleic acid can be cloned into such an expression vector such that the fusion moiety is linked in-frame to the SIX1 protein.

An isolated SIX1 protein, or fragment thereof, can be used as ah immunogen to generate antibodies that bind SIX1 using standard techniques for polyclonal and monoclonal antibody preparation. The full-length SIX1 protein can be used or, alternatively, the invention provides antigenic peptide fragments of SIX1 for use as immunogens. The antigenic peptide of SIX1 comprises at least 8 amino acid residues of the amino acid sequence shown in SEQ ID NO: 2 and encompasses an epitope of SIX1 such that an antibody raised against the peptide forms a specific immune complex with SIX1. Preferably, the antigenic peptide comprises at least 10 amino acid residues, more preferably at least 15 amino acid residues, even more preferably at least 20 amino acid residues, and most preferably at least 30 amino acid residues. Antigenic polypeptides comprising at least 50, 100, 150, 200 or 250 amino acid residues are also within the scope of the present invention. For example, an antigenic polypeptide which includes 102 amino acids of SIX1 (e.g., amino acids 183 to 284 of SEQ ID NO:2) is within the scope of the present invention. Preferred epitopes encompassed by the antigenic peptide are regions of SIX1 that are located on the surface of the protein, e.g., hydrophilic regions. Other preferred antigenic polypeptides include portions of SIX1 which do not share significant homology with other homeobox proteins (e.g., non-SIX1 proteins).

A SIX1 immunogen typically is used to prepare antibodies by immunizing a suitable subject, (e.g., rabbit, goat, mouse or other mammal) with the immunogen. An appropriate immunogenic preparation can contain, for examples, recombinantly expressed SIX1 protein or a chemically synthesized SIX1 peptide. The preparation can further include an adjuvant, such as Freund's complete or incomplete adjuvant, or similar immunostimulatory agent. Immunization of a suitable subject with an immunogenic SIX1 preparation induces a polyclonal anti-SIX1 antibody response. The immunogen can further include a portion of non-SIX1 polypeptide, for example, a polypeptide useful to facilitate purification.

Accordingly, another aspect of the invention pertains to anti-SIX1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as SIX1. The invention provides polyclonal and monoclonal antibodies that bind SIX1. The term "monoclonal antibody" or "monoclonal antibody composition", as used herein, refers to a population of antibody molecules that contain only one species of an antigen binding site capable of immunoreacting with a particular epitope of SIX1. A monoclonal antibody composition thus typically displays a single binding affinity for a particular SIX1 protein with which it immunoreacts.

Polyclonal anti-SIX1 antibodies can be prepared as described above by immunizing a suitable subject with a SIX1 immunogen. The anti-SIX1 antibody titer in the immunized subject can be monitored over time by standard techniques, such as with an enzyme linked immunosorbent assay (ELISA) using immobilized SIX1. If desired, theantibody molecules directed against SIX1 can be isolated from the mammal (e.g.. from the blood) and further purified by well known techniques, such as protein A chromatography-to obtain the IgG fraction. At an appropriate time after immunization. e.g., when the anti-SIX1 antibody titers are highest, antibody-producing cells can be obtained from the subject and used to prepare monoclonal antibodies by standard techniques, such as the hybridoma technique originally described by Kohler and Milstein (1975. *Nature* 256:495–497) (see also. Brown et al. (1981) *J. Immunol* 127:539–46: Brown et al. (1980) *J. Biol Chem* 255:4980–83; Yeh et al. (1976) PNAS 76:2927–31: and Yeh et al. (1982) Int. J. Cancer 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R.

Liss, Inc., pp, 77–96) or trioma techniques. The technology for producing monoclonal antibody hybridomas is well known (see generally R. H. Kenneth, in *Monoclonal Antibodies. A New Dimension In Biological Analyses*, Plenum Publishing Corp., New York, N.Y.(1980); E. A. Lerner (1981) *Yale J. Biol. Med.*, 54:387–402: M. L. Gefter et al. (1977) *Somatic Cell Genet.*, 3:2331–36). Briefly, an immortal cell line (typically a myeloma) is fused to lymphocytes (typically splenocytes) from a mammal immunized with a SIX1 immunogen as described above, and the culture supernatants of the resulting hybridoma cells are screened to identify a hybridoma producing a monoclonal antibody that binds SIX1.

Any of the many well known protocols used for fusing lymphocytes and immortalized cell lines can be applied for the purpose of generating an anti-SIX1 monoclonal antibody (see, e.g., G. Galfre et al. (1977) Nature 266:55052; Gefter el al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed).

Hybridoma cells producing a monoclonal antibody of the invention are detected by screening the hybridoma culture supernatants for antibodies that bind SIX1, e.g, using a standard ELISA assay.

Alternative to preparing monoclonal antibody-secreting hybridomas, a monoclonal anti-SIX1 antibody can be identified and isolated by screening a recombinant combinatorial immunoglobulin library (e.g., an antibody phage display library) with SIX1 to thereby isolate immunoglobulin library members that bind SIX1. Kits for generating and screening phage display libraries are commercially available (e.g., the Pharmacia *Recombinant Phage Antibody System*, Catalog No, 27-9400-01: and the Stratagene *SurfZAP™ Phage Dis-*

*play Kit*, Catalog No, 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay el al. (1992) *Hum Antibod Hybridomas* 3:81–85; Huse et al. (1989) *Science* 246:1275–1281; Griffiths et al. (1993) *EMBO J.* 12:725–734; Hawkins et al. (1992) *J. Mol Biol* 226:889–896; Clarkson et al. (1991) Nature 352:624–628; Gram et al. (1992) *PNAS* 89:3576–3580; Garrad et al. (1991) *Bio/Technology* 9:1373–1377; Hoogenboom et al. (1991) *Nuc Acid Res* 19:41333–4137; Barbas et al. (1991) *PNAS* 88:7978–7982; and McCafferty et al. *Nature* (1990) 348:552–554.

Additionally, recombinant anti-SIX1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi. European Patent Application 171,496: Morrison et al. European Patent Application 173,494; Neuberger et al. PCT Application WO 86/01533; Cabilly et al. U.S. Pat. No. 4.816.567; Cabilly et al. European Patent Application 125,023; Better el al. (1988) *Science* 240: 1041–1043; Liu el al. (1987) *PNAS* 84:3439–3443; Liu et al.(1987) *J. Immunol,* 139:3521–3526; Sun et al. (1987) *PNAS* 84:214–218: Nishimura el al. (1987) *Canc. Res,* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoevan et al. (1988) *Science* 239:1534: and Beidler et al.(1988) *J. Immunol,* 141:4053–4060.

An anti-SIX1 antibody (e.g., monoclonal antibody) can be used to isolate SIX1 by standard techniques, such as affinity chromatography or immunoprecipitation. An anti-SIX1 antibody can facilitate the purification of natural SIX1 from cells and of recombinantly produced SIX1 expressed in host cells. Moreover, an anti-SIX1 antibody can be used to detect SIX1 protein (e.g., in a cellular lysate or cell supernatant). Detection may be facilitated by coupling (i.e., physically linking) the antibody to a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine. dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

IV. Uses and Methods of the Invention

As described in more detail in Example 2, SIX1 expression correlates with tumorogenesis and metastasis (e.g., breast tumorigenesis and metastasis) Accordingly, detection of SIX1 protein or nucleic acid molecules provides is useful for diagnosing cancer and monitoring both tumor progression and metastasis. Furthermore, inhibition of SIX1 expression may result in inhibition of cancer and tumor metastasis ,(e.g., breast, colon, and lung cancer). The isolated nucleic acid molecules of the invention can be used to inhibit SIX1 protein expression (e.g, antisense SIX1 nucleic acid molecules), to detect SIX1 mRNA (e.g., SIX1 nucleic acid probes based on the nucleotide sequence of SEQ ID NO:1) and to modulate SIX1 activity, as discussed further below. Moreover, the anti-SIX1 antibodies of the invention can be used to detect and isolate SIX1 protein and modulate SIX1 activity, also discussed further below.

The invention provides a method for detecting the presence of SIX1 in a biological sample. The method involves contacting the biological sample with an agent capable of detecting SIX1 protein or nucleic acid molecules (e.g., SIX1 MRNA) such that the presence of SIX1 is detected in the biological sample. A preferred agent for detecting SIX1 mRNA is a labeled or labelable nucleic acid probe capable of hybridizing to SIX1 mRNA. The nucleic acid probe can be, for example, the full-length SIX1 cDNA of SEQ ID NO: 1, or a portion thereof, such as an oligonucleotide of at least 15, 30, 50, 100, 250 or 500 nucleotides in length and sufficient to specifically hybridize under stringent conditions to SIX1 mRNA.

A preferred agent for detecting SIX1 protein is a labeled or labelable antibody capable of binding to SIX1 protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As used herein, the term "isolated", when used in the context of a biological sample, is intended to indicate that the biological sample has been removed from the subject. In one embodiment, a biological sample comprises a sample which has been isolated from a subject and is subjected to a method of the present invention without further processing or manipulation subsequent to its isolation. In another embodiment, the biological sample can be processed or manipulated subsequent to being isolated and prior to being subjected to a method of the invention. For example, a sample can be refrigerated (e.g., stored at 4° C.), frozen (e.g., stored at −20° C, stored at −135° C. frozen in liquid nitrogen, or cryopreserved using any one of many standard cryopreservation techniques known in the art). Furthermore, a sample can be purified subsequent to isolation from a subject and prior to subjecting it to a method of the present invention. As used herein, the term "purified" when used in the context of a biological sample, is intended to indicate that at least one component of the isolated biological sample has been removed from the biological sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a tissue or tumor sample can be purified such that substantially only the protein or mRNA component of the biological sample remains.

Furthermore, it may be desirable to amplify a component of a biological sample such that detection of the component is facilitated. For example, the mRNA component of a biological sample can be amplified (e.g., by RT-PCR) such that detection of SIX1 mRNA is facilitated. As used herein, the term "RT-PCR" (an abbreviation for reverse transcriptase-polymerase chain reaction) involves subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase for its amplification action. Alternative amplification methods include: self sustained sequence replication (Guatelli. J. C. et al., 1990, Proc. Natl. Acad. Sci. USA 87:1874–1878), transcriptional amplification system (Kwoh. D. Y. et al., 1989. Proc. Nat]. Acad. Sci. USA 86:1173–1177), Q-Beta Replicase (Lizardi, P. M. et all, 1988. Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

The detection methods of the present invention can be used to detect SIX1 protein or nucleic acid molecules in a biological sample in vitro as well as in vivo. For example, in vitro techniques for detection of SIX1 mRNA include Northern hybridizations and in situ hybridizations. In vitro techniques for detection of SIX1 DNA include Southern hybridizations. In vitro techniques for detection of SIX1 protein include enzyme linked immunosorbent assays (ELISAs), Western blots, immunoprecipitations and immunofluorescence. Alternatively, SIX1 protein can be detected in vivo in a subject by introducing into the subject a labeled anti-SIX1 antibody. For example, the antibody can be labeled with a radioactive marker whose presence and location in a subject can be detected by standard imaging techniques.

In a preferred embodiment of the detection method, the biological sample is a tissue sample or tumor sample. The tissue sample or tumor sample may comprise tissue or a suspension of cells. A tissue section, for example, a freeze-dried, parafin-embedded, or fresh frozen section of tissue removed from a patient, or a section of a tumor biopsy can be used as the biological sample. Moreover, the sample may include a biological fluid obtained from a subject (e.g., blood, ascites, pleural fluid or spinal fluid). Following collection, tissue or tumor samples can be stored at temperatures below −20° C. to prevent degradation until the detection method is to be performed. In one embodiment, a biological sample in which SIX1 mRNA or protein is to be detected is a mammary tumor sample. In another embodiment, a biological sample in which SIX1 mRNA is to be detected is, for example, a lung, colon, or cervical tumor.

The detection methods of the invention described above can be used as the basis for a method of diagnosis of a subject with a tumor (e.g., a breast tumor), can be used as the basis for a method of monitoring the progression of cancer in a subject, or can be used as the basis for a method of prognosing a person at risk for developing a cancer. As described in further detail in Example 2, the expression pattern of SIX1 mRNA can differ between normal cells and malignant cells and between primary tumor cells and metastatic tumor cells. For example, SIX1 mRNA levels are detectable in tissues (e.g., skeletal muscle, pituitary gland, salivary gland, lung and trachea) but was not detectable in normal mammary tissue. SIX1 mRNA levels were elevated in 44% of primary breast tumors analysed and further elevated in 90% of metastatic lesion examined. In one embodiment, the invention features a method of determining the metastatic potential of a tumor which involves contacting a sample of the tumor (or isolate) with an agent capable of detecting SIX1 polypeptide or mRNA such that the presence of SIX1 polypeptide or mRNA is detected in the tumor sample or isolate, thereby determining the metastatic potential of the tumor. Another aspect of the invention features a prognostic method for determining whether a subject is at risk for developing cancer which involves contacting a biological sample obtained from the subject (or isolate of the sample) with an agent capable of detecting SIX1 polypeptide or mRNA such that the presence of SIX1 polypeptide or mRNA is detected in the biological sample or isolate, thereby determining whether the subject is at risk for developing cancer. Yet another aspect of the invention features a method of diagnosing cancer in a subject which involves contacting a biological sample obtained from the subject (or isolate of the sample) with an agent capable of detecting SIX1 polypeptide or mRNA such that the presence of SIX1 polypeptide or mRNA is detected in the biological sample or isolate, thereby diagnosing cancer in the subject. In another embodiment, the diagnostic methods of the present invention further involve determining the level of SIX1 polypeptide or mRNA in the sample or isolate. In yet another embodiment, the diagnostic methods of the present invention involve comparing the level of SIX1 polypeptide or mRNA in the sample or isolate with the level of SIX1 polypeptide or mRNA in a control sample. In yet another embodiment, the diagnostic or prognostic methods further include the step of forming a prognosis or forming a diagnosis.

In one embodiment, the control is from normal cells and the tumor sample is a suspected primary tumor sample. Primary malignancy of the tumor cell sample can be diagnosed based on an increase in the level of expression of SIX1 mRNA or protein in the tumor sample as compared to the control. In another embodiment, the control is from normal cells or a primary tumor and the tumor sample is a suspected metastatic tumor sample. Acquisition of the metastatic phenotype by the suspected metastatic tumor sample can be diagnosed based on an increase in the level of SIX1 mRNA or protein in the tumor sample compared to the control.

The prognostic methods of the present invention are of particular utility in the early detection and treatment of breast cancer. It will be appreciated by those skilled in the art that breast cancer may not be as amenable to early detection as, for instance, cervical cancer, due to the lack of cytomorphologic screening methods available (e.g., pap smears for the detection of cellular abnormalities of the cervix). Accordingly, the prognostic methods of the present invention feature, for example, careful histological examination of breast biopsies (e.g., biopsies of pre-malignant or pre-invasive lesions, atypical hyperplasias and/or carcinoma in situ). Upon the morphological detection of such a lesion, hyperplasia or carcinoma, it may be desirable to utilize an amplification step of the present invention to detect, for example, SIX nucleic acid.

The invention also encompasses kits for detecting the presence of SIX1 in a biological sample (e.g., a tumor sample). For example, the kit can comprise a labeled or labelable agent capable of detecting SIX1 protein or mRNA in a biological sample and a z means for determining the amount of SIX1 in the sample. The agent can be packaged in a suitable container. The kit can further comprise a means for comparing the amount of SIX1 in the sample with a standard and/or can further comprise instructions for using the kit to detect SIX1 mRNA or protein.

Another aspect of the invention pertains to methods of modulating SIX1 activity associated with a cell, e.g., for therapeutic purposes. SIX1 activity "associated with a cell" is intended to include SIX1 activity within the cell and/or within the nucleus of the cell. In particular, HSIX1 is a homeobox gene that is diferentially expressed in the cell cycle and whose overexpression leads to an abrogation of the DNA damage-induced G2 cell cycle checkpoint. Accordingly, in a preferred embodiment, the invention pertains to methods of modulating SIX1 activity in a subject afflicted with a disease associated with G2 checkpoint control. Such diseases include, but are not limited to Ataxia telangiectasia (Scott et al. (1994) Int. J. Radiat. Biol. 66, Suppl., 157 s–163s and Paules et al. (1995) Cancer Res, 55:1763–1773). Li Fraumeni (Paules et al, supra), Bloom's Syndrome (Davey et al.(1998) Mol. Cell. Biol, 18:2721–2728), and Fanconi Anemia (D'Andrea and Kupfer (1996) Blood 88:1019–1025), as well as other diseases which demonstrate cancer susceptibility. The modulatory method of the invention involves contacting the cell with an agent that modulates SIX1 activity associated with the cell. In one embodiment, the agent stimulates SIX1 activity. Examples of such stimulatory agents include active SIX1 protein and a nucleic acid molecule encoding SIX1 that has been introduced into the cell. In another embodiment, the agent inhibits the SIX1 activity. Examples of such inhibitory agents include antisense SIX1 nucleic acid molecules and anti-SIX1 antibodies. These modulatory methods can be performed in vitro (e.g., by culturing the cell with the agent) or, alternatively, in vivo (e.g, by administering the agent to a subject).

Inhibition of SIX1 activity is desirable in situations in which SIX1 is abnormally upregulated and/or in which decreased SIX1 activity is likely to have a beneficial effect. One example of such a situation is in tumor cells, and in particular in inhibiting or preventing tumor cell metastatis. As demonstrated in Example 2, acquisition of a metastatic phenotype by tumor cells is associated with upregulation of SIX1 expression. Thus, decreasing the expression and/or activity of SIX1 in or around the tumor cells is expected to inhibit the development or progression of the metastatic phenotype. Accordingly, in a specific embodiment, the invention provides a method for inhibiting development or progression of a metastatic phenotype in a tumor cell comprising contacting the tumor cell with an agent which inhibits the amount of SIX1 in the tumor cell. The term "in the tumor cell" is intended to include SIX1 within the cell and/or SIX1 within the nucleus of the cell. For example, since SIX1 is predicted to be a transcription factor, it is likely that it exerts tumor suppressive effects nuclearly. The agent that inhibits SIX1 in the tumor cell can be an antisense SIX1 nucleic acid or a SIX1 antibody. Thus, a SIX1 inhibitory agent, preferably in a pharmaceutically acceptable carrier, can be administered to a tumor-bearing subject by an appropriate route to inhibit the development or progression of the metastatic phenotype of the tumor. Suitable routes of administration include intravenous, intramuscular or subcutaneous injection, injection directly into the tumor site or implantation of a device containing a slow-release formulation. The SIX1 inhibitory agent preparation can also be incorporated into liposomes or other carrier vehicles to facilitate delivery to the tumor site. A non-limiting dosage range is 0.001 to 100 mg/kg/day, with the most beneficial range to be determined by routine pharmacological methods.

Alternative to administration of a SIX1 inhibitory agent, the development or progression of the metastatic phenotype can be inhibited in tumor cells by modifying them to express a SIX1 inhibitory agent (e.g., a SIX1 antisense nucleic acid molecule) by introducing into the tumor cells a SIX1 antisense nucleic acid expression vector. Expression vectors suitable for gene therapy, including retroviral and adenoviral vectors carrying appropriate regulatory elements, can be used to deliver the SIX1 antisense nucleic acids to the tumor cells.

In addition to tumor therapy, there are other situations in which modulating SIX1 activity may be desirable. As demonstrated in Example 3, SIX1 overexpression in cells results in abbrogation of the G2 cell cycle checkpoint. Accordingly, SIX1 inhibition may be desirable to reconstitute growth arrest in a population of cells, such that DNA repair can take place.

This invention is further illustrated by the following examples which should not be construed as limiting. The contents of all references, patents and published patent applications cited throughout this application are hereby incorporated by reference.

EXAMPLE 1

Figure 2A:
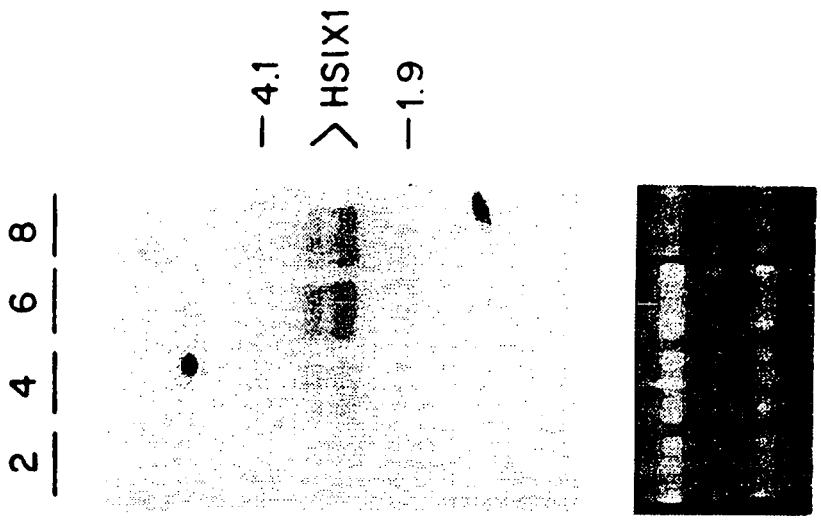
FIG. 2A–C.

Identification of HSIX1 as a Cell-Cycle Regulated Gene by Differential Display Methodology To identify genes differentially expressed in S-phase of the 21PT mammary adenocarcinoma cell line, cells were first synchronized with mimosine. Briefly, cell synchrony was performed as described (Alpan and Pardee (1996) Cell Growth Differ. 7:893–901); however, 150 µM mimosine was used rather than 400 µM. S phase syncrhonized cells were released from late G1/S phase arrest, S-phase progression was monitored by $^3$H-thymidine incorporation at hourly intervals (Keyomarsi et al. (1991) Cancer Res. 51:3602–3609) (FIG. 2A), and RNA was isolated from duplicate samples to perform differential display. Briefly, differential display was performed with a two-step pokymerase chain reaction (PCR) and the LHA series of primers as described (Martin el al. (1996) in Methods in Molecular Biology-Differential Display Methods and Protocols, eds. Pardee & Liang (Humana, Totowa, N.J.). Vol, 85, pp.[77–85]). The anchored and the arbitrary primers which led to detection of HSIX1 were LHT$_{11}$C (TGC CGA AGC T$_{11}$C) (SEQ ID NO:3) and LHA6 (TGC CGA AGC TTG CAG CGA) (SEQ ID NO:4). Band isolation and direct sequencing of the DD band were performed as described (Martin et al., stipra).

Figure 2B:
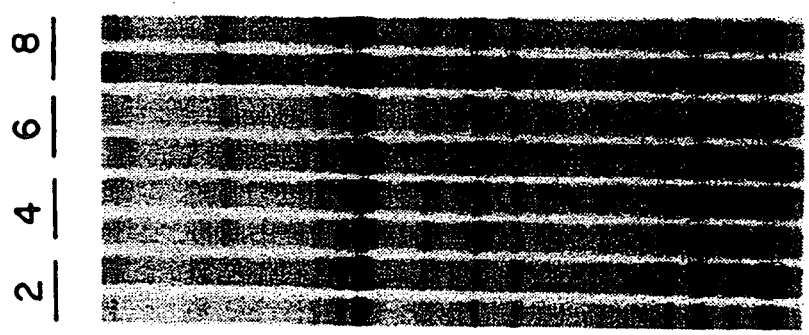
Figure 2C:
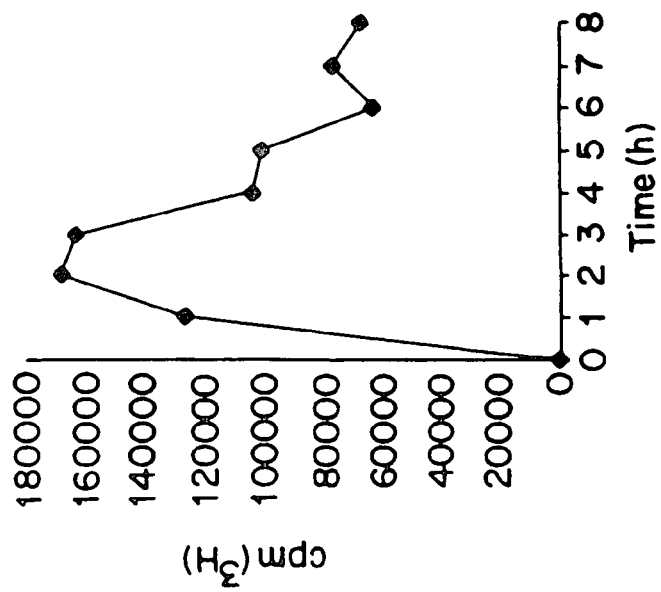

FIG. 2B demonstrates increased expression of a cDNA band labeled as 6A. Direct sequencing of 6A revealed its identify as HSIX1, a homeobox gene whose mouse counterpart has been implicated in the development of limb tendons (Oliver et al. (1995) Development 121 :693–705) and that was recently cloned from human adult skeletal muscle (Boucher et al. (1996) Genomics 33:140–142). A Northern blot probed with HSIX1 cDNA (cloned from 21PT cells by RT-PCR) confirmed its differential expression in S-phase (FIG. 2C). (Briefly, to clone HSIX1 cDNA for use as a probe, primers were designed to the 5' end (5'-ATG TCG ATG CTG CCG TCG TTT-3') (SEQ ID NO:5) and 3' end (5'-CAC TTA GGA CCC CAA GTC CAC-3') (SEQ ID NO:6) of the HSIX1 cDNA. Reverse transcription (RT) reactions were performed with 0.2 µg RNA template, 25 µMdNTPs, 1 mM DTT, 5 µM oligo $dT_{2-18}$, and 1x reverse transcriptase buffer (50 mM Tris-HCl, pH 8.3, 75 mM KCl, 3 mM>MgCl2). The reaction conditions were as follows, 65° C. , 5 min.; 37° C. , 60 min. (5 min, into this cycle 200 units SuperscriptTM II was added to each reaction); 95° C. , 5 min. PCR conditions were as follows: {94° C., 45 sec.; 69° C., 45 sec.; 72° C. , 45 sec.}×25, followed by an extension at 72° C., 5 min. The PCR products were subcloned utilizing the TA cloning system (InVitrogen). (Sequencing was performed on multiple clones as it is known that PCR may introduce point mutations.) For Northern blot analysis, RNA was isolated with TRIzol reagent and analysis was performed according to Maniatis et al. (1989) *Molecular Cloning* (Cold Spring Harbor Lab. Press, Cold Spring Harbor, N.Y.), $2^{nd}$ Ed.

Levels of HSIX1 were very low in the first half of S-phase, and increased as cells completed S phase. Similar experiments in a related cell line (21MT1), also revealed cell cycle-specific expression of the gene indicating that HSIX1 plays a role at or near the end of the cell cycle.

Additional evidence supporting a function of HSIX1 in cell cycle control can be obtained by comparison of SIX to the Drosophila *sine oculis* (*so*) gene. The HSIX1 protein displays approximately 98% sequence homology to mouse SIX1 (Boucher et al. (1996) *Genomics* 33:140–142) which was first cloned by virtue of its homology to the Drosophila gene *sine oculis* (*so*) (Oliver et al. (1995) *Development* 121:693–705). Mouse SIX1 is 62% similar to the Drosophila gene, and 87% similar if sequences C-terminal to the homeodomain are excluded (supra). So plays a role in the development of the fly visual system. Interestingly, Drosophila eye development involves coordinate regulation of cell cycle progression and so has been suggested to play a role in the synchronization of the cell cycle because its expression precedes a burst of cell divisions (Cheyette et al. (1994) *Neuron* 12:977–996). In addition, complete loss of function alleles of so are embryonic lethals (supra), suggesting that the gene's expression is important for more than just eye development. These results in conjunction with the cell cycle regulated expression of HSIX1 in 21PT cells, suggest that HSIX1 plays a role in regulating the onset of mitosis.

EXAMPLE 2

Expression of HSIX1 in Primary Tumors, Metastatic Tumors, and Other Tumor-Derived Cell Lines For comparison with 21PT mammary carcinoma cells, a Human RNA Master Blot from Clontech™ was probed to determine HSIX1 expression in normal human adult mammary tissue as well as its expression pattern in other normal adult and fetal tissues (as expression of HSIX1 and its mouse homolog had previously only been demonstrated in developing mouse limb tendons and in human adult skeletal muscle). The Human RNA Master Blot includes poly A+ RNA from the following tissues: whole brain, amygdala, caudate nucleus, cerebellum, cerebral cortex, frontal lobe, hippocampus, medulla oblongata, occipital lobe, putamen, substantia nigra, temporal lobe, thalamus, subthalamic nucleus, spinal cord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, spleen, thymus, peripheral leukocyte, lymph node, bone marrow, appendix, lung, trachea, placenta, fetal brain, fetal heart, fetal kidney, fetal liver, fetal spleen, fetal thymus, and fetal lung. Yeast total RNA (100 ng), yeast tRNA (100 ng), *E. coli* rRNA (100 ng), *E. coli* DNA (100 ng), Poly r(A) (100 ng), human $C_o$t 1 DNA (100 ng), human DNA (100 ng), and human DNA (500 ng) were included as controls.

It was determined that normal mammary tissue (pooled from 20 women ages 24–40 who died of trauma) does not express HSIX1, whereas, expression was confirmed in normal adult skeletal muscle and was also observed in pituitary gland, salivary gland, lung and trachea, with very low levels of expression in the kidney. These data further indicate that expression of HSIX1 expression in mammary carcinoma cells is aberrant.

Figure 3A:
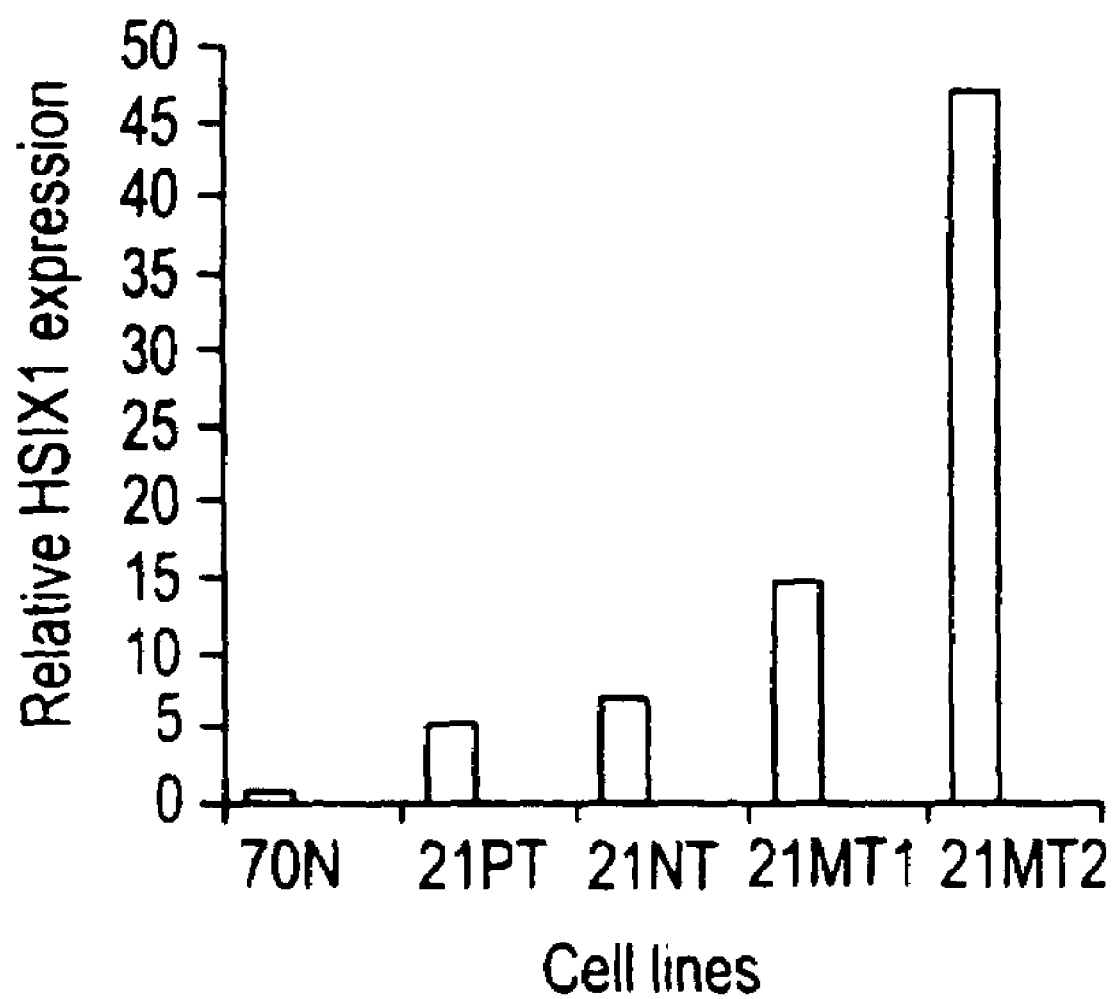
FIG. 3 is a quantitative representation of a Northern blot analysis of 3 control tissues (normal adjacent breast, normal luminal cells, and normal myoepithelial cells-lanes 1,2, and 3 respectively) as well as on 25 primary breast tumor biopsies (lanes 4–28) and 10 metastatic lesions (lanes 29–38). The blot was stripped and reprobed with 36B4 (Hatano et al.(1991) *Science* 253:79–82) for normalization and relative HSIX1 expression was plotted. A 3-fold increase over normal adjacent breast was considered positive for HSIX1 and is marked by a dashed line.
Figure 4A:
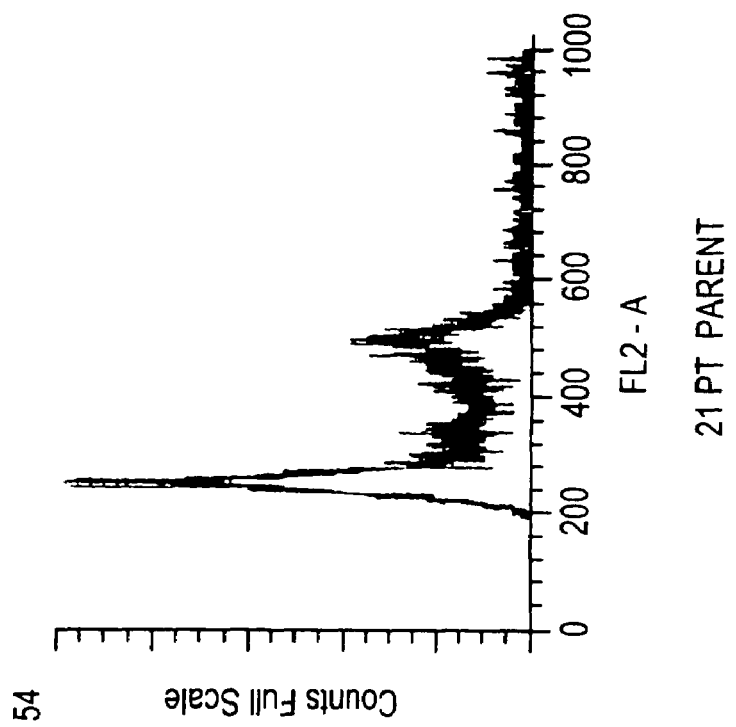
FIG. 4 depicts FACS analysis of HSIX1 overexpressors which become polyploid over several months in culture. "His/lac7 control" indicates cells transfected approximately 6 months prior to FACS analysis shown. "21PT parent" indicates cells transfected approximately 4.5 months prior to FACS analysis shown. "SIXFL4" and "SIXFL6" indicates cells transfected approximately 4 and 6 months prior to FACS analysis shown, respectively.
Figure 4B:
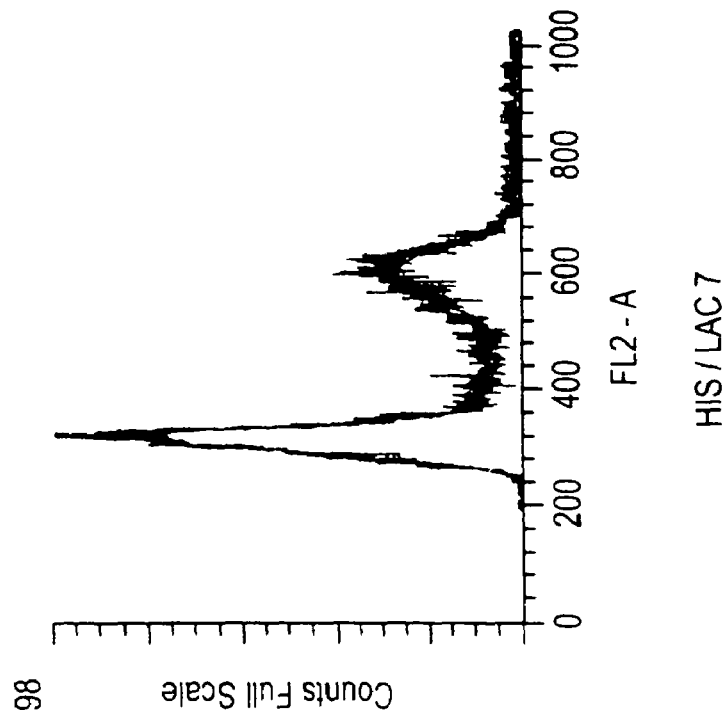
Figure 4C:
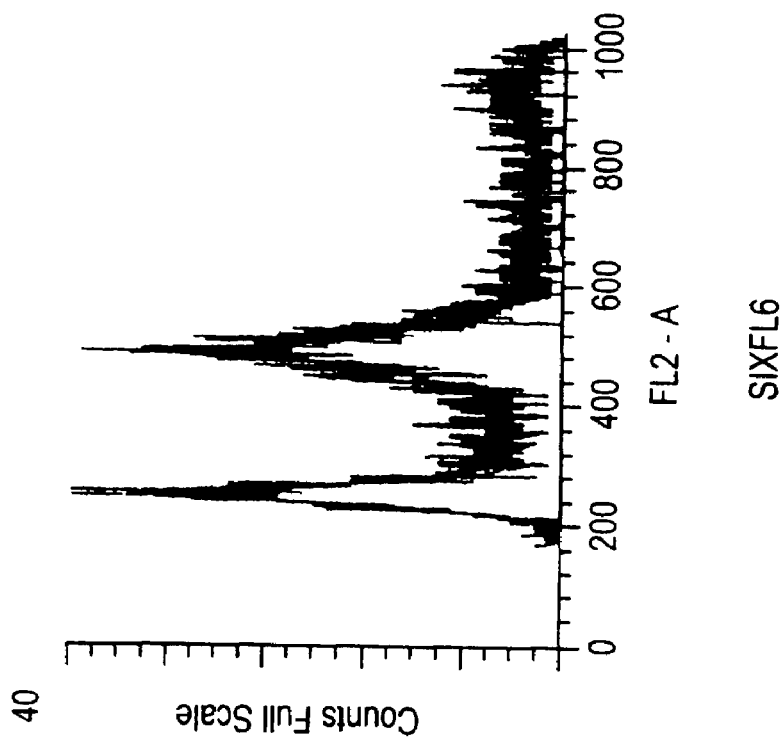
Figure 4D:
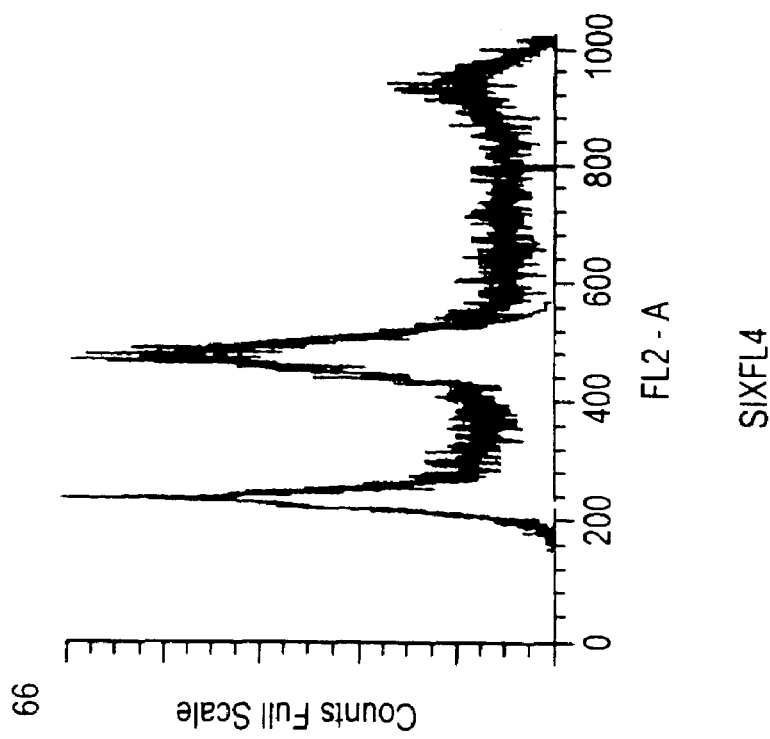

21PT cells, the source of HSIX1, were derived from a patient who had an infiltrating and intraductal mammary adenocarcinoma (Band et al. (1990) *Cancer Res.* 50:7351–7357). Several other cell lines derived from the same patient include 21 NT, 21MT-1, and 21MT-2. The 21PT and 21NT cell lines were derived from the primary tumor, whereas the 21MT-1 and 21MT-2 cell lines were established from a metastatic pleural effusion. As shown in FIG. 3, HSIX1 expression was not detected in a normal breast cell line, 70N (Band and Sager, supra), but was detected in all cell lines derived from the above-mentioned patient. Levels of expression in 21PT and 21NT cells were approximately 3- and 2-fold less, respectively, than levels in 21MT1 cells, and 10- and 7-fold less, respectively, than levels in 21MT2 cells. (Relative HSIX1 expression for each sample was as follows, 70N ~0, 21PT ~5, 21NT ~7, 21MT1 ~14, and 21MT2 ~46).

To determine whether HSIX1 expression is increased in a significant proportion of primary and metastatic breast cancer cases, 35 human breast biopsy samples were obtained and expression was examined by Northern blot analysis. Northern blot analysis was performed as described in Example 1, except that RNA was isolated from breast tumor specimens by the guanidinium thiocyanate/CsCI method as described in Maniatis et al., supra. Normalization to 36B4 was performed on these samples, as it has been shown to be a good control for breast cancer samples. FIG. 3 shows the results with 35 tumor samples examined for HSIX1 expression. The results were quantitated and plotted as relative HSIX1 expression. While normal adjacent breast, normal breast luminal cells, and normal breast myoepithelial cells demonstrated almost no HSIX1 expression (lanes 1–3 respectively). 44% of the primary tumors (lanes 4–27) and 90% of the metastatic lesions (lanes 28–37) expressed greater than a three-fold increase in HSIX1 mRNA expression over levels in normal adjacent breast.

As the metastatic lesions came from a secondary site, it was necessary to consider the expression levels of the tissue at this site to confirm that the expression observed is from the lesion and not from contaminating adjacent tissue. The 10 metastatic lesions utilized in the analysis came from either the lymph nodes (6 samples), bone/soft tissue (2 samples), the lung (1 sample), or the pleural wall (1 sample). The Human RNA Master blot allowed examination of HSIX1 expression in normal lymph nodes and lung. Five of the six lymph node metastases expressed HSIX1, however HSIX1 expression was not observed in normal lymph nodes, indicating that the high expression levels in lymph node lesions came from the metastatic tumor itself. Normal lung does express the gene at low levels, but densitometric scanning and subsequent normalization demonstrated that expression in the metastatic lesion from the lung was equal to that in normal adult skeletal muscle, which expresses four times more HSIX1 than normal lung. This suggests that HSIX1 expression in the lung metastases cannot be explained by normal tissue contaminating the sampled metastasis.

Having demonstrated the high expression in primary breast cancer tumors as well in metastatic tumors, multiple lung cancer cell lines as well as cell lines isolated from a range of other tumors, were analyzed for HSIX1 expression by Northern blot (2 μg poly(A)+ RNA isolated from each human cancer cell line, Clonetech Blot). HSIX1 expression was detected in mRNA isolated from cells of a colon adenocarcinoma of a patient (termed "SW480 cells") and was significantly enhanced in mRNA from cells isolated from a metastatic lesion of the same patient (termed "SW620 cells"). HSIX mRNA was also detected in cell lines isolated from the following tumor sources:

| CELL LINE | Tumor Source | relative HSIX1 expression |
| --- | --- | --- |
| HL-60 | promyelocytic leukemia | |
| HeLa | HeLa Cell S3 - cervical carcinoma | +++ |
| K562 | chronic myelogenous leukemia | +++ |
| MOLT4* | lymphoblastic leukemia | |
| Raji | Burkitt's lymphoma | + |
| SW480 | colorectal adenocarcinoma | +++ |
| A549 | lung carcinoma | ++ |
| G361 | melanoma | + |

*Inadequate RNA loading may be responsible for absence of HSIX1 expression in MOLT4.

Furthermore, HSIX1 mRNA was demonstrated to be overexpressed in multiple lung cancer cells. When six pairs of cell line mRNAs were analyzed for HSIX1 expression, the first sample being isolated from a lung tumor, and the second sample being isolated from normal adjacent tissue of the same patient, HSIX1 expression was found to increase from 1.5 to 10-fold, among the various tumor-derived samples tested, as compared to their normal counterparts. Collectively, the above-described data indicate that HSIX1 is overexpressed in several types of cancer in addition to breast.

EXAMPLE 3

Overexpression of HSIX1 in Cells Abrogates the G2 Cell Cycle Checkpoint

To determine if HSIX1 plays a role in regulating the cell cycle, the MCF7 mammary carcinoma cell line was transfected with SIXFL, a construct that allows for constitutive expression of the full length wild type HSIX1 cDNA, or with the parent vector expressing the chloramphenicol acetyl transferase gene (CAT) as a control. MCF7 cells are mammary carcinoma cells with a lower endogenous HSIX1 level than that in 21PT cells. Briefly, MCF7 cells were seeded in 60 mM dishes at $5\times10^5$ cells/dish and transfected with SIXFL or with pcDNA3.1(CAT) utilizing Superfect (Qiagen). Transfections were performed according to the manufacturers protocol, 24 h after transfections the cells were passaged 1:15 in appropriate media containing 600 mg/ml G418. Approximately two weeks later stable transfectants were selected utilizing cloning cylinders and examined for HSIX1 expression via Northern blot analysis. For all subsequent analysis, three stable clones expressing HSIX1 (HSIXA1. A8, and A13) and two control transfectants (CATB1 and CATB3, expressing pcDNA3.1 (CAT)) were examined in the X-Ray irradiation assay.

X-Ray irradiation and subsequent FACS analysis of transfected cells was performed as follows: MCF7 transfectants were seeded at $8\times10^5$ cells/60 mM dish. Approximately 48 h later the cells were treated with X-rays (5 or 8 Gy) at a dose rate of 1.25 Gy/min using a Phillips 250 kVp X-ray machine. Sham treated controls as well as irradiated cells were labeled with propidium iodide according to Vindelov et al. (1983) *Cytometry* 3:323–327, at various time points following irradiation. Experiments were performed singly or in duplicate, and repeated several times. FACS analysis was performed on the Becton Dickinson FACScan utilizing CellQuest (Becton Dickinson) and ModFit (Verity Software) to obtain cell cycle profiles.

Figure 5:
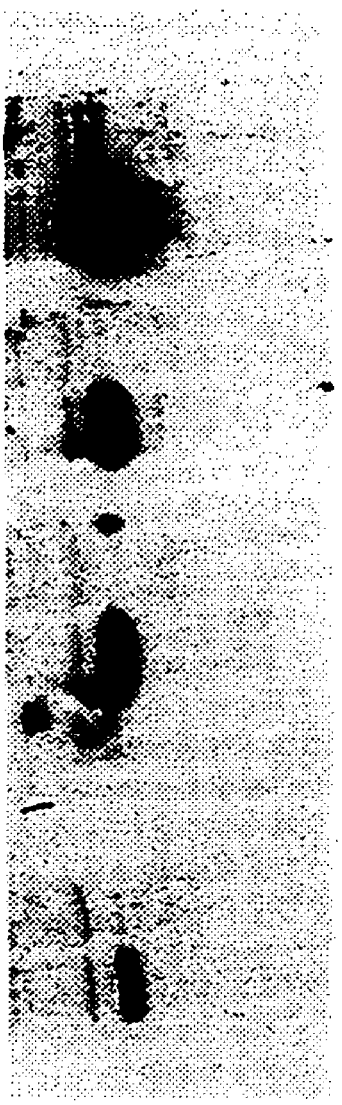
FIG. 5 is a Western Blot demonstrating the immunoreactivity of an anti-HSIX antibody with SIX protein from transfected cells. Lanes marked "T" indicate lysates of MCF7 cells transfected with HSIX1. Lanes marked "M"

In a representative experiment, exponentially growing cells overexpressing HSIX1 (the HSIXA13 cell line) showed cell cycle profiles similar to the transfected control (the CATB3 cell line) (HSIXA13: G1=55.1%, S=26.9%, G2/M=18.1% versus CATB3: G1=53.2%, S=31.3%, G2/M=15.5%). In contrast, when the cells were irradiated at a dose of 8 Gy to examine the DNA damage-induced G2 cell cycle checkpoint, a marked difference was observed in the G2/M population in HSIX1 transfectants versus the CAT controls. In the representative experiment, both HSIX1 expressors and CAT controls were arrested in G2 17 h after irradiation, as was expected (HSIXA13: G1=49.8%, S=6.8%, G2/M=43.5% versus CATB3: G1=57.1%, S=6.9%, G2/M=36%). However, by 24 h post-irradiation, all cell lines expressing HSIX1 had progressed beyond the G2 arrest, whereas the non-expressors remained arrested in G2 (HSIXA13: G1=75.5%, S=4.9%, G2/M=19.6% versus CATB3: G1=60.2%, S=5.6%. G2/M=34.2%). The CAT control transfectants were blocked in G2 as long as 30 h post-irradiation, whereas the HSIX1 transfectants had exited the G2 arrest significantly earlier (HSIXA13: G1=74.6%. S=5.4%, G2/M=20.0% versus CATB3: G1=58.7%. S=5.3%, G2/M=36%). Although absolute percentages varied from experiment to experiment, the passage of HSIX1 expressors through G2 following X-ray irradiation was always more rapid than that of the controls. Note that MCF7 cells have an intact G1/S arrest in response to irradiation, and that cells passing through G2 will subsequently arrest at the G1/S boundary. A summary of data collected from several experiments is presented as FIG. 5. In particular, FIG. 5 depicts a summary of the percentage of cells in G2 at various time points before and after irradiation in the transfectants and controls. The data graphed are from one experiment performed at 8 Gy and are representative of several experiments performed at 5 and 8 Gy. Note that cells expressing HSIX1 progress through the G2 arrest at a more rapid rate than transfected controls.

In addition to the CAT controls, a cell line transfected with SIXFL (HSIXA2) that did not express HSIX1 (possibly due to silencing of the gene upon insertion into the chromosomal DNA) was tested in the X-ray irradiation assay. This cell line behaved as the CAT controls, confirming that HSIX1 expression was necessary for abrogation of the G2 cell cycle checkpoint, and that the expression of CAT did not affect the checkpoint in any way. Furthermore, it was generally observed that the growth rates of the HSIX1 transfectants and controls in the absence of irradiation were not appreciably different, indicating that the rapid transit of HSIX1 transfectants through the G2 arrest following DNA damage was not merely a consequence of faster growth. These data demonstrate that overexpression of HSIX1 leads to an abrogation of the DNA damage-induced G2 cell cycle checkpoint.

In yet another series of experiments, 21PT cells were transfected with HSIX1 or an HSIX1 fusion protein that contains an 8 amino acid epitope tag (XPRESS) for following protein expression. Immunohistochemistry of the latter transfectants with the anti-XPRESS antibody revealed a punctate nuclear localization of the HSIX1 protein, as is commonly observed with proteins involved in replication and/or transcription. The result was expected, as HSIX1 is a putative transcription factor. Moreover, after passaging the cells over several months, a change in the DNA content of the transfectants was observed. FIG. 4 shows a representative FACS analysis on propidium iodide stained SIXFL4 and 6 cells and the His/lac7 and parent 21PT control cells. The DNA content in the HSIX1 expressing transfectants doubled in a large proportion of the cells, whereas the doubling was not observed in the control cells passaged over an even longer time period. This analysis demonstrates that HSIX overexpressors become polyploidy over several months in culture, further demonstrating an effect at the level of cell cycle control.

Interestingly, another homeobox gene. HOX11, has recently been found to disrupt the G2 cell cycle checkpoint by interacting with PP2A protein phosphatase (Kawabe et al. (1997) *Nature* 385:454–458). HOX11 has been implicated in cancer (supra), as it was isolated from a chromosomal breakpoint in human T-cell leukemia (Hatano et al. (1991) *Science* 253:79–82; Kennedy et al. (1991) *Proc. Natl. Acad Sci. USA* 88:8900–8904: and Dube et al. (1991) *Blood* 78:2996–3002). In addition, transgenic mice expressing HOX11 in the thymus demonstrated cell cycle alterations and progression to malignancy (Hatano et al. (1992) *Curr. Opin. Oncol* 4:24–26). Since HSIX1 was originally cloned from a mammary carcinoma cell line (21PT), and since overexpression of this gene leads to altered cell cycle control similar to that seen with HOX11, it can be reasoned that HSIX1 may be differentially expressed in cancer.

EXAMPLE 4

Generation of HSIX1-Specific Antibodies

The C-terminus of HSIX1 (from nucleotide 822 until the stop codon) was amplified and subcloned into the pGEX2T bacterial expression vector to create a GST-HSIX1 fusion protein. Expression of the protein was induced with 0.1 mM IPTG, and the protein was then purified from bacterial extracts utilizing glutathione-sepharose beads. Following purification, the fusion protein was run on a SDS-PAGE gel, very lightly coomassie stained, and extracted from the gel.

The extracted gel piece containing the GST-HSIX1 C-terminus was then injected into rabbits (Spring Valley Laboratories (Woodbine, Md.)). Following injection and two boosts, the rabbit was bled and the sera tested for HSIX1 antibodies. Following demonstration of HSIX1 immunoreactivity, the sera was passed over a GST affinity column (to remove any antibody recognizing the GST portion of the fusion), and was subsequently purified on a GST-HSIX C-terminus column. Affinity purified anti-HSIX1 antibody was then tested on cells transfected with HSIX1 versus untransfected cells (FIG. 6).

EXAMPLE 5

HSIX1 Expressing Cells Lead to Larger Tumors When Injected Into Nude Mice

Six nude mice each were injected in the thigh with either $1 \times 10^7$ A13 cells (HSIX-transfected) or B3 cells (control transfectants). Tumor size was measured after 4.5 weeks. Tumors from B3 cells-injected mice ranged in size from approximately 35–140 $mm^3$ whereas tumors from A13 cell-injected mice ranged in size from approximately 110–370 $mm^3$ (Table I).

TABLE I

| Control Transfectants | HSIX1-Transfected |
| --- | --- |
| 53.2 | 365.9 |
| 138.5 | 112.8 |
| 76.2 | 208.7 |
| 35.5 | 194.0 |
| 95.4 | 282.9 |
| 91.1 | 110.6 |

These data demonstrate the significant tumorigenic activity of HSIX1.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of determining the metastatic potential of a tumor comprising:
   (a) contacting a tumor sample, or isolate thereof, with an antibody that specifically binds to a human SIX1 polypeptide or a nucleic acid probe that specifically hybridizes to a human SIX1 nucleic acid molecule under stringent conditions, comprising hybridization in 6X SSC at about 45° C., followed by one or more washes in 0.2X SSC, 0.1% SPS at 50–65° C., such that expression of the SIX1 polypeptide or nucleic acid molecule is detected in the tumor sample or isolate; and
   (b) comparing the expression of SIX1 in the sample or isolate to a standard or control, wherein increased expression of SIX1 relative to the standard or control is determinative of the metastatic potential of the tumor, wherein the antibody specifically binds to a polypeptide selected from the group consisting of:
      (1) a polypeptide comprising SEQ ID NO:2;
      (2) a polypeptide comprising at least amino acids 183–284 of SEQ ID NO:2, which is at least 95% homologous to SEQ ID NO:2, and has the ability to enhance cell cycle progression; and
      (3) a polypeptide consisting of amino acids 183–284 of SEQ ID NO:2; and
   wherein the human SIX1 nucleic acid molecule encodes a biologically active human SIX1 polypeptide, and is selected from the group consisting of a nucleic acid molecule consisting of the nucleotide sequence of SEQ ID NO:1, a nucleic acid molecule comprising at least nucleotides 276 to 1130 of SEQ ID NO:1, and a nucleic acid molecule encoding a polypeptide consisting of the amino acid sequence of SEQ ID NO:2.

2. A prognostic method for determining whether a subject is at risk for developing cancer comprising:
   (a) contacting a biological sample obtained from the subject, or isolate of the sample, with an antibody that specifically binds to a human SIX1 polypeptide or a nucleic acid probe that specifically hybridizes to a human SIX1 nucleic acid molecule under stringent conditions, comprising hybridization in 6X SSC at about 45° C. followed by one or more washes in 0.2X SSC, 0.1% SDS at 505° C., such that expression of the SIX1 polypeptide or nucleic acid molecule is detected in the sample or isolate; and
   (b) comparing the expression of SIX1 in the sample or isolate to a standard or control, wherein increased expression of SIX1 relative to the standard or control is determinative of the subject being at risk for developing cancer,
   wherein the antibody specifically binds to a polypeptide selected from the group consisting of:
      (1) a polypeptide comprising SEQ ID NO:2;
      (2) a polypeptide comprising at least amino acids 182–284 of SEQ ID NO:2, which is at least 95% homologous to SEQ ID NO:2, and has the ability to enhance cell-cycle progression; and (3) a polypeptide consisting of amino acids 183–284 of SEQ ID NO:2; and wherein the human SIX1 nucleic acid molecule encodes a biologically active human SIX1 polypeptide, and is selected from the group consisting of a nucleic acid molecule consisting of the nucleotide sequence of SEQ ID NO: 1, a nucleic acid molecule comprising at least nucleotides 276 to 1130 of SEQ ID NO: 1, a nucleic acid molecule consisting of nucleotides 276 to 1130 of SEQ ID NO:1, and a nucleic acid molecule encoding a polypeptide consisting of the amino acid sequence of SEQ ID NO:2.

3. A method for diagnosis of a tumor comprising:

(a) contacting a suspected tumor sample, or isolate thereof, with an antibody capable that specifically binds to a human SIX1 polypeptide or a nucleic acid probe that specifically hybridizes to a human SIX1 nucleic acid molecule under stringent conditions, comprising hybridizaton in, 6X SSC at about 45° C. followed by one or more washes in 0.2X SSC, 0.1% SDS at 50–65° C., such that expression of the SDC1 polypeptide or nucleic acid molecule is detected in the sample or isolate; and (b) comparing the expression of SIX1 in the sample or isolate to a standard or control, wherein increased expression of SIX1 relative to the standard or control is diagnostic of the tumor, wherein the antibody specifically binds to a polypeptide selected from the group consisting of:

(1) a polypeptide comprising SEQ ID NO:2;

(2) a polypeptide comprising at least amino acids 183–284 of SEQ ID NO:2. which is at least 95% homologous to SEQ ID NO:2, and has the ability to enhance cell cycle progression; and (3) a polypeptide consisting of amino acids 183–284 of SEQ ID NO:2; and wherein the human SIX1 nucleic acid molecule encodes a biologically active human SIX1 polypeptide, and is selected from the group consisting of a nucleic acid molecule consisting of the nucleotide sequence of SEQ ID NO:1, a nucleic acid molecule comprising at least nucleotides 276 to 1130 of SEQ ID NO: 1, a nucleic acid molecule consisting of nucleotides 276 to 1130 of SEQ ID NO: 1, and a nucleic acid molecule encoding a polypeptide consisting of the amino acid sequence of SEQ ID NO:2.

4. A method of diagnosing cancer in a subject comprising:

(a) contacting a biological sample obtained from the subject, or isolate of the sample, with an antibody that specifically binds to a human SIX1 polypeptide or a nucleic acid probe that specifically hybridizes to a human SIX1 nucleic acid molecule under stringent conditions, comprising hybridization in 6X SSC at about 45° C., followed by one or more washes in 0.2X SSC, 0.1% SDS at 50–65° C., such that expression of the SIX1 polypeptide or nucleic acid molecule is detected in the sample or isolate; and (b) comparing the expression of SIX1 in the sample or isolate to a standard or control, wherein increased expression, of SIX1 relative to the standard or control is diagnostic of cancer in the subject, wherein the antibody specifically binds to a polypeptide selected from the group consisting of:

(1) a polypeptide comprising SEQ ID NO:2;

(2) a polypeptide comprising at least amino acids 183–284 of SEQ ID NO:2, which is at least 95% homologous to SEQ ID NO:2, and has the ability to enhance cell cycle progression; and (3) a polypeptide consisting of amino acids 183–284 of SEQ ID NO:2; and wherein the human SIX1 nucleic acid molecule encodes a biologically active human SIX1 polypeptide, and is selected from the group consisting of a nucleic acid molecule consisting of the nucleotide sequence of SEQ ID NO: 1, a nucleic acid molecule comprising at least nucleotides 276 to 1130 of SEQ ID NO: 1, a nucleic acid molecule consisting of nucleotides 276 to 1130 of SEQ ID NO:1, and a nucleic acid molecule encoding a polypeptide consisting of the amino acid sequence of SEQ ID NO:2.

5. A method for monitoring the progression of cancer in a patient comprising:

(a) contacting a biological sample obtained from the patient, or isolate of the sample, with an antibody that specifically binds to a human SIX1 polypeptide such that expression of the SIX1 polypeptide is detected in the biological sample; and (b) comparing the expression of SIX1 in the sample to a standard or control, wherein increased expression of SIX1 relative to the standard or control is an indicator of cancer progression, and wherein the SIX1 polypeptide is selected from the group consisting of:

(1) a polypeptide comprising SEQ ID NO:2;

(2) a polypeptide comprising at least amino acids 183–284 of SEQ ID NO:2, which is at least 95% homologous to SEQ ID NO:2, and has the ability to enhance cell cycle progression; and (3) a polypeptide consisting of amino acids 183–284 of SEQ ID NO:2.

6. A method for monitoring the progression of cancer in a patient comprising:

(a) contacting a biological sample obtained from the patient, or isolate of the sample, with a nucleic acid probe that specifically hybridizes to a human SIX1 nucleic acid molecule under stringent conditions, comprising hybridization in 6X SSC at about 45° C., followed by one or more washes in 0.2X SSC, 0.1% SDS at 50–65° C. such that expression of the nucleic acid molecule is detected in the biological sample; and (b) comparing the expression of SIX1 in the sample to a standard or control, wherein increased expression of SIX1 relative to the standard or control is an indicator of cancer progression, and wherein the nucleic acid molecule encodes a biologically active human SIX1 polypeptide, and is selected from the group consisting of a nucleic acid molecule consisting of the nucleotide sequence of SEQ ID NO: 1, a nucleic acid molecule comprising at least nucleotides 276 to 1130 of SEQ ID NO, 1, a nucleic acid molecule consisting of at least nucleotides 276 to 1130 of SEQ ID NO:1, and a nucleic acid molecule encoding a polypeptide consisting of the amino acid sequence of SEQ ID NO: 2.

7. The method of any one of claims 5, 6, 2 and 4, wherein the biological sample is a tissue sample, or isolate thereof.

8. The method of claim, wherein the tissue sample is derived from the pancreas, stomach, liver, secretory gland, bladder, lung, skin, prostate gland, ovary, cervix, uterus, brain, eye, connective tissue, bone, muscles or vasculature.

9. The method of any one of claims 5, 6, 2 and 4 wherein the biological sample is a breast tissue sample, or isolate thereof.

10. The method of any one of claims 5, 6, 2 and 4, wherein the biological sample is a tumor sample, or isolate thereof.

11. The method of claim 10, wherein the tumor sample is selected from the group consisting of a lung carcinoma, a colon carcinoma, a cervical carcinoma, an adenocarcinoma, a melanoma, a leukemia, a lymphoma, a glioma, a neuroblastoma, a retinoblastoma, and a sarcoma.

12. The method of claim 10, wherein the tumor sample is a breast tumor sample.

13. The method of claim 5, 6, wherein the biological sample is a primary tumor sample, or isolate thereof.

14. The method of claim 5, 6, wherein the biological sample is a metastatic lesion sample, or isolate thereof.

15. The method of any one of claims 5, 6 and 1–4, wherein the antibody is labeled.

16. The method of claim 15, wherein the antibody is a polyclonal antibody.

17. The method of any one of claims 5, 6 and 1–4, wherein the nucleic acid probe is labeled.

18. The method of claim any one of claims 5, 6, 2 and 4, wherein the biological sample is a tissue sample isolate, the isolate being RNA which is subjected to an amplification process.

19. The method of any one of claims 5, 6, 2 and 4, wherein the biological sample is a biological fluid.

20. The method of claim 19, wherein the biological fluid is blood or serum.

21. The method of claim 20, wherein the biological fluid is blood.

22. The method of claim 2 or 4, wherein the biological sample is a biological fluid.

23. The method of claim 22, wherein the biological fluid is blood or serum.

24. The method of claim 23, wherein the biological fluid is blood.

25. The method of claim 1, wherein the tumor sample is selected from the group consisting of a lung carcinoma, a colon carcinoma, a cervical carcinoma, an adenocarcinoma, a melanoma, a leukemia, a lymphoma, a glioma, a neuroblastoma, a retinoblastoma, and a sarcoma.

26. The method of claim 1, wherein the tumor sample is a breast tumor sample.

* * * * *